(12) United States Patent
Cowing

(10) Patent No.: US 7,229,621 B2
(45) Date of Patent: *Jun. 12, 2007

(54) METHOD TO ENHANCE THE IMMUNOGENICITY OF AN ANTIGEN

(75) Inventor: Carol O. Cowing, Del Mar, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 09/809,158

(22) Filed: Mar. 15, 2001

(65) Prior Publication Data

US 2001/0024649 A1    Sep. 27, 2001

Related U.S. Application Data

(63) Continuation-in-part of application No. 09/176,044, filed on Oct. 20, 1998, now Pat. No. 6,210,672.

(51) Int. Cl.
*A61K 39/00*    (2006.01)
*A61K 45/00*    (2006.01)

(52) U.S. Cl. ................. 424/184.1; 424/278.1

(58) Field of Classification Search ............ 424/278.1, 424/184.1
See application file for complete search history.

(56) References Cited

U.S. PATENT DOCUMENTS

| | | | |
|---|---|---|---|
| 4,036,952 A * | 7/1977 | Bauer et al. | |
| 4,353,896 A | 10/1982 | Levy | |
| 4,455,142 A | 6/1984 | Martins et al. | |
| 4,683,200 A | 7/1987 | Hirohashi et al. | |
| 4,861,589 A | 8/1989 | Ju | |
| 5,202,130 A | 4/1993 | Grant et al. | |
| 5,278,263 A | 1/1994 | Burroway | |
| 5,316,920 A | 5/1994 | Tedder et al. | |
| 5,487,897 A | 1/1996 | Polson et al. | |
| 5,654,312 A | 8/1997 | Andrulis, Jr. et al. | |
| 5,910,306 A | 6/1999 | Alving et al. | |
| 5,980,898 A * | 11/1999 | Glenn et al. | |
| 6,797,276 B1 | 9/2004 | Glenn et al. | |

FOREIGN PATENT DOCUMENTS

| EP | 0 308 210 | | 3/1989 |
|---|---|---|---|
| GB | 2 145 931 | | 4/1985 |
| WO | WO 88/00001 | * | 1/1988 |
| WO | WO 91/04030 | * | 4/1991 |
| WO | WO 94/17827 | * | 8/1994 |
| WO | WO 97/04832 | * | 2/1997 |
| WO | WO 98/20734 | | 5/1998 |
| WO | WO 00/35351 | * | 6/2000 |

OTHER PUBLICATIONS

Marchal et al (Adv Exp Med Biol, 1995, vol. 378, pp. 219-221).*
King et al (Vaccine, 1987, vol. 5, pp. 234-238).*
Stricker et al (Immunology Letters, 1991, vol. 29, pp. 191-196).*
Girolomoni et al (Journal of Immunology, 1983, vol. 150, pp. 4236-4243).*
Paul et al (Vaccine Research, 1995, vol. 4, pp. 145-164).*
Roitt et al, Immunology (text), 1993, pp. 8.3-8.4.*
Dearman et al (Fundamental and Applied Toxicology, 1996, vol. 33, pp. 24-30).*
Salyers et al (Bacterial Pathogenesis (text), 1994, pp. 8-14 and 144-145).*
Streitwieser and Heathcock, Introduction to Organic chemistry, (text), 1976, pp. 643-645.*
Baumann et al (Journal of Immunology, 2000, vol. 165, pp. 158-167).*
Price et al (Journal of Experimental Medicine, 1997, vol. 186, pp. 1725-1735).*
International Search Report for PCT/US98/07817.
Yechiel Becker, Dengue Fever Virus and Japanese Encephalitis Virus . . . , Virus Genes 9:1, pp. 33-45 (1994).
Yechiel Becker, An Analysis of the Role of Skin Langerhans Cells (LC in the Cytoplasmic Processing of HIV-1 Peptides . . . , Virus Genes 9:2, pp. 132-147 (1994).
James W. Young, et al., Dendritic Cells as Adjuvants for Class I Major Histocompatibility Complex-Restricted Antitumor Immunity, J. Exp. Med. vol. 183, pp. 7-11 (1996).
Laurence Zitvogel, et al., Therapy of Murine Tumors with Tumor Peptide-pulsed Dendritic Cells, J. Exp. Med., vol. 183, pp. 87-97 (1996).
Christina Celluzzi, et al., Peptide-Pulsed Dendritic Cells Induce Antigen-specific CTL-Mediated Protective Tumor Immunity, J. Exp. Med., vol. 183, pp. 283-287 (1996).
Paola Paglia, et al., Murine Dendritic Cells Loaded in Vitro with Soluble Protein . . . , J. Exp. Med., vol. 183, pp. 317-322 (1996).
Samir Mitragotri, et al., Ultra-sound Mediated Transdermal Protein Delivery, Science. vol. 269, pp. 850-853 (Aug. 1995).
Jacques Banchereau, et al., Dendritic Cells and the Control of Immunity, Nature, vol. 293, pp. 245-252.
Kenjiro Matsuno, et al., A Life Stage of Particle-laden Rat Dendritic Cells In Vivo . . . , J. Exp. Med., vol. 183, pp. 1865-1878 (Apr. 1996).
M.C. Udey, Cadherins and Langerhans Cell Immunobiology, Clin Exp Immunol, vol. 107 (Suppl. 1), pp. 6-8 (1997).
A. Larregina, et al., Flow Cytometric Analysis of Cytokine Receptors on Human Langerhans Cells, Immunoloty, vol. 87 pp. 317-325 (1996).
B. Wang, et al., Tumour Necrosis Factor Reception II . . . , Immunology, vol. 88, pp. 284-288 (1996).
Aimin Tang, et al., Suppression of Murine Allergic Contact Dermatitis . . . , The Journal of Immunology, vol. 157, pp. 117-125 (1996).

(Continued)

*Primary Examiner*—Karen A. Canella
(74) *Attorney, Agent, or Firm*—Knobbe, Martens, Olson & Bear, LLP

(57) ABSTRACT

The present invention is related to a method for enhancing the immunogenicity of an antigen in a mammal by introducing into the mammal an antigen or a portion thereof and administering to the mammal a treatment that increases antigen presentation in a lymphoid organ.

17 Claims, 14 Drawing Sheets

OTHER PUBLICATIONS

Vanbever, et al., "Transdermal Delivery of Metoprolol by Electroporation", Pharmaceutical Research, vol. 11, No. 11, 1994.

Suzuki, H., et al. (1998) Imiquimod, A Novel Topical Immune Response Modifier Induces Migration of Langerhans (Abstract) Cells. J. Invest. Dermatol. 110(4):566.

Sauder, D. N. (2000) Immunomodulatory and Pharmacologic Properties of Imiquimod. J. Am. Acad. Dermatol. 43:S6-S11.

Enk A.H. et al. 1993 "An essential role of Langerhans cell-derived IL-1β in the initiation of primary immune response in skin," J. Immunol. 150:3698-3704.

Supplemental European Search Report from corresponding application EP 98 91 8392, mailed on Oct. 21, 2004.

Koyama et al. (1989) Effect of systemic and topical application of testosterone propionate on the density of epidermal Langerhans cells in the mouse. J. Invest. Dermatol. 1:86-90 (Abstract).

Murphy et al. (1998) Tropical tretinoin replenishes CD1a-positive epidermal Langerhans cells in chronically photodamaged human skin. J. Cutan. Pathol. 1:30-4 (Abstract).

Ragg et al. (1994) Lagerhans cell migration patterns from sheep skin following topical application of carcinogens. Int. J. Exp. Pathol. 1:23-8.

* cited by examiner

Intravaginal Application of Peptide and DBP Induces Protective Tumor Immunity

Tumor Specific Immunity Induced by Cutaneous Application of Tumor Peptide in concentrated DMSO followed by DBP Lymph Node Dendritic Cells Induced by Topical Application of Dibutylphthalate Analogs Antigen-bearing Dendritic Cells in Lymph Nodes after Injection of Soluble Protein or Peptide followed by Migration Inducer Tumor-specific Immunity induced by a Single Injection of a Tumor Protein followed by a Topical Migration Inducer

Adjuvant Effects of Inducing Dendritic Cell Migration/Maturation

METHOD TO ENHANCE THE IMMUNOGENICITY OF AN ANTIGEN

RELATED APPLICATIONS

This application is a continuation-in-part of pending U.S. patent application Ser. No. 09/176,044 filed on Oct. 20, 1998 now U.S. Pat. No. 6,210,672, and claims priority thereto under 35 U.S.C. §120.

Research related to this invention was supported in part by a grant from the National Institutes of Health to Lancell, LLC; accordingly, the United States Government has certain rights in this invention.

BACKGROUND OF THE INVENTION

In principle, the adaptive immune response can provide protective immunity to almost any non-self substance. In spite of this enormous potential, only a few dozen effective vaccines currently exist in the face of countless infectious agents, tumors, and disease processes that might be controlled by the induction of immunity to the pathogenic entity. Two factors are involved in determining a vaccine's efficacy: 1) the use of antigenic epitopes able to confer protective immunity, and 2) immunogenicity, or the capacity of the vaccine to induce an immune response to the antigens contained therein. In the last decade, it has become increasingly clear that the immunogenicity of an antigen depends largely on its presentation by dendritic cells.

Dendritic cells are not only the most potent antigen-presenting cells identified to date, but apparently the only ones that can activate naive (previously unstimulated) T cells in a primary immune response (Banchereau and Steinman 1998 Nature 392:245–252). Activation of naive T cells is necessary if a vaccine is to produce full T cell immunity and optimal antibody responses. Dendritic cells have this capacity due to their expression of high levels of the ligands required to activate naive T cells—namely, MHC:peptide complexes, co-stimulatory molecules and intercellular adhesion molecules (Sprent 1999 J Immunol. 163:4629–4636).

The problem for vaccine development is that dendritic cells are rare. They comprise approximately 1/400 cells in secondary lymphoid organs, 1/500 white blood cells and <1/1000 cells in most non-lymphoid organs. Their scarcity is compounded by the low frequency of naive T cells able to respond to any single antigenic epitope, or MHC:peptide complex, estimated to be $1/10^5$ to $1/10^4$ (Mason 1998 Immunol. Today 19:395–404). Hence, induction of an immune response depends upon antigen reaching one rare cell that must then interact with another rare cell, which would seem to militate against the development of immunity.

Naive T cells continuously recirculate through lymph nodes via the bloodstream (Gretz et al. 1996 J. Immunol. 157:495–499), whereas immature dendritic cells are relatively stable residents of non-lymphoid organs (Cowing and Gilmore 1992 J. Immunol. 148:1072–1079). Immature dendritic cells express low levels of surface MHC and co-stimulatory molecules and, as such, are only weak stimulators of T cell activation. However, these cells are actively pinocytic and phagocytic, enabling them to sample their environment for the presence of potential pathogens. When exposed to appropriate stimuli, immature dendritic cells are mobilized. Local tissue-specific adhesion molecules are down-regulated, permitting the cells to disengage from the tissue and migrate via afferent lymphatics to draining lymph nodes (Banchereau and Steinman 1998 Nature 392:245–252).

During their migration to lymph nodes, immature dendritic cells undergo "maturation" to become potent inducers of T cell activation. Maturation is characterized by 1) down-regulation of pinocytosis and phagocytosis, and 2) increased surface expression of MHC molecules that are loaded with peptides newly derived from proteins recently taken up from the environment. The expression of co-stimulatory molecules and intercellular adhesion molecules is up-regulated during maturation, while the pattern of chemokine receptor expression is altered, enabling the migrating dendritic cells to follow the correct route to the paracortical, T cell-rich areas of the draining lymph node (Banchereau and Steinman 1998 Nature 392:245–252). Once induced to migrate from their tissue of residence to the regional lymph node, mature antigen-bearing dendritic cells will be positioned to be encountered by antigen-specific naive T cells present in the recirculating pool of lymphocytes.

Langerhans cells are perhaps the best studied of the immature dendritic cells and serve as a prototype of immature dendritic cells in non-lymphoid organs. They reside in the epidermal layer of the skin and mucous membranes, where they are present in higher frequency (i.e., 1 to 2%) than the immature dendritic cells found in other non-lymphoid organs. Langerhans cells are bound to neighboring keratinocytes via the homophilic adhesion molecule E-cadherin (Udey 1997 Clin. Exp. Immunol. 107(Suppl. 1):6–8). This bond must be attenuated before the Langerhans cell can become mobile. Signals known to mobilize immature dendritic cells (e.g., IL-1, TNF-α, and LPS) have also been shown to decrease the expression of E-cadherin on Langerhans cell-like dendritic cells, inducing the loss of E-cadherin-mediated adhesion (Jakob and Udey 1998 J. Immunol. 160:4067–4073). Once released from surrounding keratinocytes, Langerhans cells pass through the basement membrane of the epidermis into the dermis, enter afferent dermal lymphatics and migrate to skin-draining lymph nodes. As detailed above, during this migration, Langerhans cells mature to acquire very high levels of surface MHC, co-stimulatory and adhesion molecules, and begin to express chemokines that attract naive T cells (Banchereau and Steinman 1998 Nature 392:245–252). Once in the draining lymph node, Langerhans cells remain there for a few days and then disappear (Ruedl et al. 2000 J. Immunol. 165: 4910–4916).

Whether mature antigen-bearing dendritic cells will be encountered by and activate naive T cells in the lymph node is likely to depend on three factors: 1) the number of antigen-bearing dendritic cells that enter the node, 2) the density of MHC:peptide complexes expressed on their membranes, and 3) the frequency of antigen-specific T cells in the recirculating pool. Activation of naive T cells is a stochastic process, and the magnitude of the response increases with increasing density of MHC:peptide complexes on the antigen-presenting cell (Reay et al. 2000 J. Immunol. 164: 5626–5634; Wherry et al. 1999 J. Immunol. 163:3735–3745). Similarly, the initial encounter between a dendritic cell and a naive antigen-specific T cell is most likely stochastic and should increase with increasing frequency of either cell type. For example, an administration of antigen that resulted in no detectable interaction between antigen-bearing dendritic cells and antigen-specific T cells in normal mice, was found to be immunogenic in mice that had an artificially high frequency of antigen-specific T cells (approximately $1/10^3$) due to the transfer of T cells containing an antigen-specific T cell receptor transgene (Manickasingham and Reis e Sousa 2000 J. Immunol.

165:5027–5034). Based on the preceding considerations, a critical component of vaccine immunogenicity is the capture of vaccine antigens by rare, immature dendritic cells and the induction of their maturation and migration to draining lymph nodes, in numbers sufficient to be encountered by rare, antigen-specific T cells.

The induction of dendritic cell migration is a complex process that is incompletely understood at present, but certain signals have the capacity to mobilize or induce the migration of immature dendritic cells from their tissue of residence. They include the pro-inflammatory cytokines, TNF-α and IL-1, and bacterial lipopolysaccharide (LPS) (Kimber et al. 2000 *Brit. J. Derm.* 142:401–412). These signals, along with GM-CSF and other cytokines, initiate the maturation process as well. Physical trauma to a tissue, such as surgical excision, also may induce the migration and maturation of resident immature dendritic cells (Steinman et al. 1995 *J. Invest. Dermatol.* 105:2S–7S).

The paucity and functional immaturity of dendritic cells in non-lymphoid organs may explain why injection of an aqueous solution of most protein or peptide antigens results in little or no immunity and can even result in immunologic tolerance (Davila and Celis 2000 *J. Immunol.* 165:539–547; Garza et al. 2000 *J. Exp. Med.* 191:2021–2027; Liblau et al. 1997 *Immunol. Today* 18:599; Weiner 1997 *Immunol. Today* 18:335). Only a few dendritic cells are likely to be exposed to the antigen; and, in the absence of a stimulus for dendritic cell migration and maturation, those cells may never reach regional lymph nodes for recognition by recirculating T cells. Conversely, if the antigen is presented by cells that lack co-stimulatory and adhesion molecules, antigen-specific T cell tolerance can ensue. Genetic vaccines, comprising DNA or RNA encoding the antigen(s), also require processing of the protein product by host dendritic cells (Iwasaki et al. 1997. *J. Immunol.* 159:11) and thus are subject to the same constraints.

In summary, there is a need for an effective method to a) promote the capture of vaccine antigens by rare, immature dendritic cells, and b) induce the maturation of antigen-loaded dendritic cells and their migration to draining lymph nodes, in numbers sufficient to be encountered by rare, antigen-specific T cells. Such a method would function as an adjuvant to generate an adaptive immune response to an otherwise weak or non-immunogenic administration of antigen.

SUMMARY OF THE INVENTION

The present invention is related to a method for vaccinating a mammal against an antigen. The method comprises introducing into the mammal an effective dose of the antigen or an epitope(s) thereof, and administering to the mammal a topical treatment in an amount sufficient to increase the number of antigen-bearing dendritic cells in a draining lymphoid organ, wherein introducing the antigen and administering the treatment are performed independently in any order.

In accordance with one preferred mode of the invention, the topical treatment may comprise a lipophilic molecule capable of traversing the stratum corneum and inducing immature dendritic cells to migrate to the draining lymphoid organ. This lipophilic molecule may be selected from the following formulas:

(1)

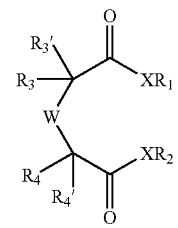

(2)

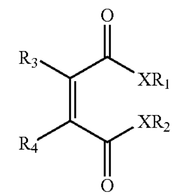

(3)

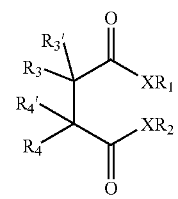

wherein $R_1$ and $R_2$ are independently alkyl side chains containing 1 to 16 carbon atoms, $C_1$ to $C_{16}$ substituted alkyl, $C_3$ to $C_{10}$ cycloalkyl, $C_3$ to $C_{10}$ substituted cycloalkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl;

wherein $R_3$, $R_3'$, $R_4$ and $R_4'$ are selected independently from the group consisting of hydrogen atom, hydroxy group, halogeno group, alkyl side chains containing 1 to 16 carbon atoms, $C_1$ to $C_{16}$ substituted alkyl, $C_3$ to $C_{10}$ cycloalkyl, $C_3$ to $C_{10}$ substituted cycloalkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_7$ to $C_{16}$ phenylalkyl, $C_7$ to $C_{16}$ substituted phenylalkyl, phenyl, substituted phenyl, naphthyl and substituted naphthyl;

wherein X is an oxygen or a nitrogen atom; and wherein W is a saturated or unsaturated chain consisting of $C_1$–$C_{10}$ alkyl, $C_1$–$C_{10}$ substituted alkyl, $C_7$–$C_{10}$ phenylalkyl, $C_7$–$C_{16}$ substituted phenylalkyl, phenyl, substituted phenyl, naphthyl, substituted naphthyl, $C_3$–$C_7$ cycloalkyl and $C_3$–$C_7$ substituted cycloalkyl group, and wherein each terminus of the chain is bonded to the carbon $C(R_3R_3')$ and $C(R_4R_4')$.

In variations to the lipophilic molecule, W may contain one or more heteroatoms selected from the group consisting of nitrogen, sulfur, and oxygen in combination or independently.

In another variation to the lipophilic molecule, the $R_1$ and $R_2$ groups may be identical $C_1$ to $C_6$ alkyl moieties. The $R_1$ and $R_2$ may be $(CH_2)_3$—$CH_3$.

In another variation to the lipophilic molecule, X may be an oxygen and $R_3$ and $R_4$ are linked to form a ring structure which, including the W chain, comprises saturated or unsaturated $C_3$ to $C_{10}$ cycloalkyl, $C_3$ to $C_{10}$ substituted cycloalkyl, $C_7$ to $C_{16}$ phenylalkyl, $C_7$ to $C_{16}$ substituted phenylalkyl, phenyl, substituted phenyl, naphthyl or substituted naphthyl. The ring structure may be an aryl group. The ring structure may also contain one or more heteroatoms selected from the group consisting of nitrogen, sulfur, and oxygen.

In another variation the lipophilic molecule may comprise a terpene.

In another variation, the lipophilic molecule may be selected from the group consisting of dibutyl phthalate, dibutyl-D-tartarate, N,N-diethyl-toluamide, dibutylfumarate, di(2-ethylhexyl)fumarate, diisooctylmaleate, diethylhexylmaleate, diisooctylfumarate, benzoic acid, bihenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, diethylmethylphthalate and camphor.

Preferably, the lipophilic molecule is <500 daltons. The lipophilic molecule also preferably has an oil/water partition coefficient >1 and more preferably, between about 10 and about $10^6$.

In another variation, the topical treatment may also comprise an organic solvent, which may be acetone.

Alternatively, or in addition, the topical treatment of the present method may comprise application of ultrasound energy.

The antigen or epitope(s) thereof may be introduced into the mammal by any of a variety of means, for example, by: a virus, bacterium, fungus, or parasite; by ingestion; by disrupting the stratum corneum; by injection (via a route selected from the group consisting of intraepidermal, intradermal, subcutaneous, intramuscular, intravascular, or into a specific organ); by delivery to at least a portion of the respiratory, urogenital, or gastrointestinal tracts; by a transfer of cells containing the antigen or epitope(s) thereof; by transformation of a cell within the mammal and expression of the antigen or epitope(s) thereof by the transformed cell; and by the transfer of a nucleic acid encoding the antigen or epitope(s) thereof. The antigen or epitope(s) thereof may be endogenous to the mammal and may be either normal or pathologic (e.g., tumor).

In another variation to the method of the invention, the amount of topical treatment administered to the mammal may be sufficient to increase the number of antigen-bearing dendritic cells in the lymphoid organ by a factor of about 2 to about 1000 times the number of resident dendritic cells in the untreated mammal. In another variation, the number of antigen-bearing dendritic cells in the lymphoid organ may be increased by a factor of about 5 to about 100 times the number of resident dendritic cells. Alternatively, or in addition, the amount of topical treatment may also be characterized as: being sufficient to increase local release of an endogenous inducer of dendritic cell migration and maturation; or being sufficient to alter the plasma membrane expression or function of an adhesion molecule.

Another method of immunization is disclosed in the present application, comprising introducing into the mammal an expression vector adapted to induce the prolonged expression of the antigen or epitope thereof, and administering a topical treatment to the mammal during a period when the antigen is being expressed, wherein the topical treatment is administered in an amount sufficient to increase the number of antigen-bearing dendritic cells in a lymphoid organ. The antigen or epitope(s) thereof may be endogenous to the mammal (e.g., a tumor antigen). The topical treatment in accordance with this mode may be administered repeatedly at periodic intervals during the period when the antigen is being expressed.

In one mode, the topical treatment is a lipophilic molecule capable of traversing the stratum corneum and inducing immature dendritic cells to migrate to the draining lymphoid organ. In another mode, the topical treatment may comprise application of ultrasound energy.

In another variation of the present invention, a method is disclosed for vaccinating a mammal against an antigen. The method comprises injecting into the mammal an effective dose of the antigen or an epitope(s) thereof, and administering to the mammal a topical treatment in an amount sufficient to increase the number of antigen-bearing dendritic cells in a draining lymphoid organ, wherein the topical treatment comprises a lipophilic molecule with a molecular weight of <500 daltons.

In another variation of the present invention, a method is disclosed for enhancing an immune response in a mammal against an endogenous antigen such as a tumor antigen. The method comprising repeated topical application to the mammal of a lipophilic compound having a molecular weight <500 daltons, wherein the lipophilic compound is applied in an amount sufficient to increase the number of antigen-bearing dendritic cells in a lymphoid organ.

In another variation of the present invention, a method is disclosed for vaccinating a mammal against an antigen. The method comprises delivering to the mammal a nucleic acid vaccine, comprising a DNA or RNA encoding the antigen or an epitope(s) thereof, and administering to the mammal a topical treatment in an amount sufficient to increase the number of antigen-bearing dendritic cells in a lymphoid organ, wherein the topical treatment comprises a lipophilic molecule with a molecular weight of <500 daltons.

In another variation of the present invention, a method is disclosed for vaccinating a mammal against an antigen. The method comprises providing the mammal with an effective dose of the antigen or an epitope(s) thereof, and administering internally to the mammal a treatment in an amount sufficient to increase the number of antigen-bearing dendritic cells in a lymphoid organ. Internal administration routes may include injection, delivery to an organ or delivery to the gastrointestinal, respiratory and/or urogenital tracts. The treatment may comprise a lipophilic molecule with a molecular weight of <500 daltons or low frequency ultrasound energy.

DETAILED DESCRIPTION OF THE PREFERRED EMBODIMENT

Figure 1:
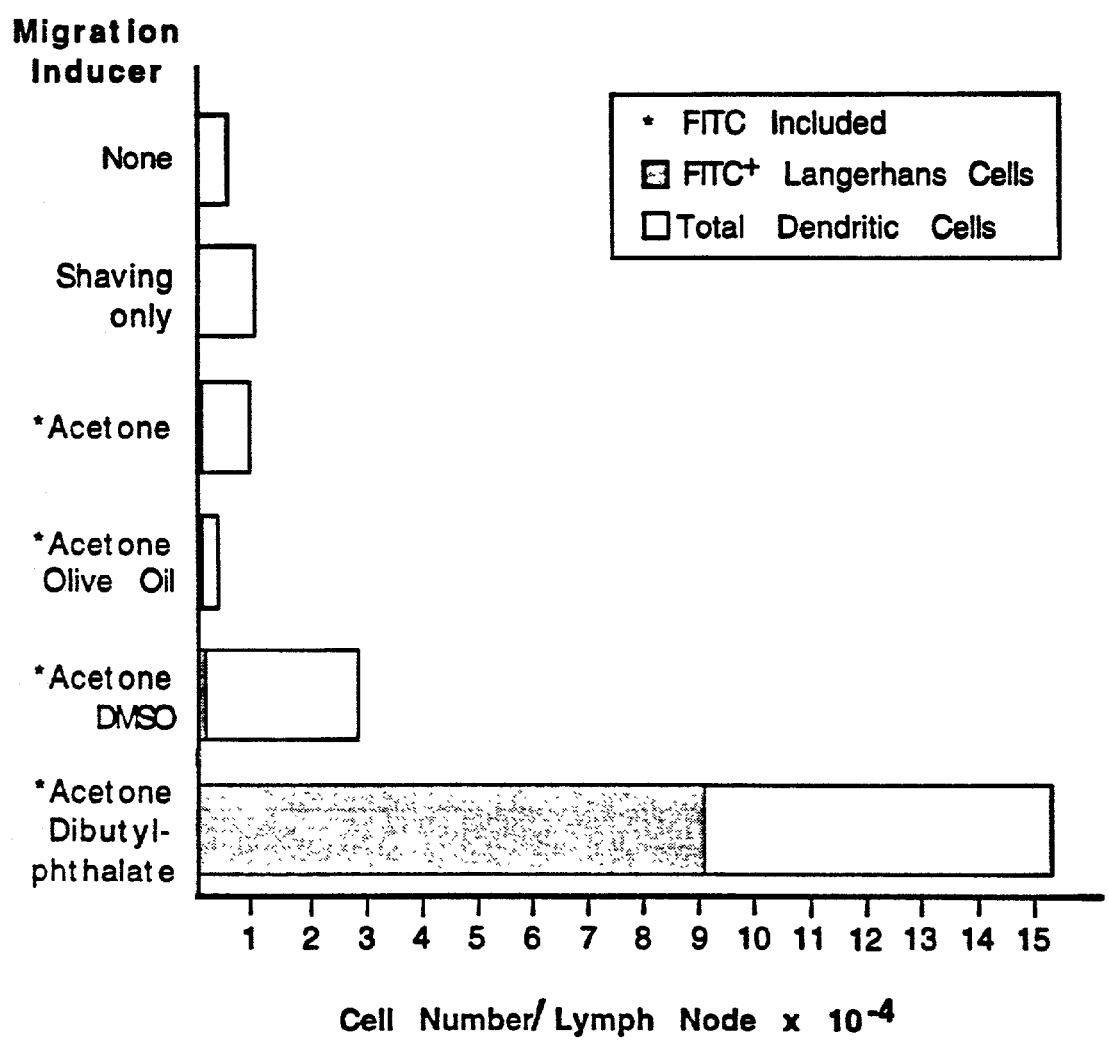
FIG. 1 illustrates the effect of various topical treatment regimens on total and FITC+ dendritic cells in the draining lymph node 2 days after treatment.

The following terms shall have the definitions set out herein. "Adaptive immunity" refers to the response to antigen by lymphocytes bearing clonally-distributed, antigen-specific receptors. The term "antigen" means any substance capable of being recognized by the adaptive immune system. "Epitope" refers to the site on an antigen recognized by an antigen-specific receptor on cells of the adaptive immune system. The term "immunogenicity" means the capacity to induce an immune response. An "immunogen" is an antigen in a form that induces an immune response. The term "vaccine" refers to the antigen(s) used to deliberately stimulate an adaptive immune response by immunization. An "adjuvant" is a substance or treatment that enhances the immunogenicity of an antigen. The "innate immune response" refers to the early phase of the host response to infection, mediated by cells that lack antigen-specific receptors but respond to molecular patterns common to many different microbial pathogens. The term "Langerhans cell" refers to the immature dendritic cells found in the epidermal layer of the skin and mucous membranes, that serve as a prototype of the immature dendritic cells found in non-lymphoid organs. The terms Langerhans cell and immature dendritic cells are used interchangeably throughout the specification. The abbreviation "MHC" refers to "Major Histocompatibility Complex."

With respect to immunizing a mammal with an antigen, the term "introducing into" is used to encompass any means of providing the antigen into the mammal as distinguished from topical application, i.e. onto. For example, the following non-topical routes of administration are deemed to be encompassed be the term "introducing into": parenteral and peroral administration, administration via the gastrointestinal, respiratory and urogenital tracts, past the protective stratum corneum via injection or mechanical or chemical disruption of the stratum corneum (e.g., intraepidermal, intradermal, subcutaneous, intramuscular, intravascular, intramedullary injection), infection with a virus, bacterium, fungus, or parasite, transfer of cells containing the antigen, transformation of a cell within the mammal and expression of the antigen by the transformed cell.

A variety of methods to exploit the antigen-presenting function of dendritic cells are currently being tested or have been proposed. One approach is ex vivo. Dendritic cell precursors are enriched from peripheral blood, exposed to cytokines and antigen ex vivo and re-injected into the donor (Thurner et al. 1999 *J. Exp. Med.* 190:1669–1678). Since effective immunity depends on the histocompatibility molecules of the dendritic cells being the same as those of the recipient, this necessitates an individualized procedure. A second approach involves in vivo administration of colony stimulating factors, such as Flt3 ligand, in order to increase the output of dendritic cells from precursors in the bone marrow (reviewed in Antonysamy and Thomson 1999 *Cytokine* 12:87–100). The expectation is that this will increase dendritic cell processing and presentation of tumor antigens in vivo, thereby enhancing tumor-specific immunity.

Whole microorganisms are strong immunogens, while vaccines comprised of their isolated protein or carbohydrate antigens often lack sufficient immunogenicity to be clinically useful (Edelman 1997 In New Generation Vaccines. Marcel Dekker, New York, N.Y. p. 173–192). Microbial products have been used experimentally as immunologic adjuvants for many years, but their mechanism of action is only now being elucidated. Microbial components, such as lipopolysaccharide, lipoproteins, peptidoglycans, and unmethylated cytosine-guanosine oligonucleotide sequences found predominantly in bacterial DNA, are recognized by Toll-like, pattern-recognition receptors of the innate immune response (reviewed in Aderem and Ulevitch 2000 *Nature* 406:782–787). Dendritic cells, as members of the innate immune system that also initiate adaptive immunity, are sensitive to activation by microbial stimuli (Reis e Sousa et al. 1999 *Curr. Opin. Immunol.* 11:392). Thus, the use of microbial components to enhance the immunogenicity of vaccines may function at least in part by activating dendritic cells (Manickasingham and Reis e Sousa 2000 *J. Immunol.* 165:5027–5034). Unfortunately, these same microbial components are pro-inflammatory and can contribute to the development of septic shock (Modlin 2000 *Nature* 408: 659–660).

In addition to bacteria, certain viruses can influence the function of dendritic cells. For example, immature dendritic cells residing at mucosal surfaces are the most likely initial cellular targets for HIV. These cells become infected with HIV and then transfer the virus to T cells in the draining lymph node (Weissman and Fauci 1997 *Clin. Microbiol. Rev.* 10:358–367). Some viral infections have been reported to activate dendritic cells, e.g., vaccinia virus (Hernando et al. 1994 *Immunol. Cell Biol.* 72:383–389) and arboviruses (Johnston et al. 2000 *J. Invest. Dermatol.* 114:560–568). Just as often, infection of dendritic cells with viruses either inhibits dendritic cell function, e.g., HSV-1 (Kruse et al. 2000 *J. Virol.* 74:7127–7136), or subverts dendritic cells to cause generalized immunosuppression, e.g., Rauscher leukemia virus (Gabrilovitch et al. 1994 *Immunology* 82:82–87) and measles virus (Bhardwaj 1997 *J. Exp. Med.* 186:795–799).

Some proposed methods to recruit dendritic cells involve chemotactic chemokines that attract migrating dendritic cells to a particular location. WO 00/03728 suggests the use of chemokines, such as MIP-1α, MIP-3α and RANTES, to attract migrating dendritic cells to sites of antigen deposition. WO 0009151 proposes a means of achieving a similar effect using agonists of CCR7, the receptor for the chemokines 6Ckine and MIP-3α on dendritic cells. Chemokines are physiologic attractants of dendritic cells that are already mobile or migrating, but neither of these approaches has been shown to induce or initiate the migration of immature dendritic cells that are stable residents of non-lymphoid tissues.

Some treatments have been reported to alter the route taken by migrating dendritic cells. Enioutina et al. expanded dendritic cells in cultures of murine bone marrow, incubated the cells with cholera toxin, Forskolin, or the active form of vitamin D3, and then injected the cells into the skin of naive recipients (Enioutina et al. 2000 *Vaccine* 18:2753–2767). These pretreatments resulted in preferential localization of the injected cells to gut-associated Peyer's patches. The route taken by the culture-derived cells from the site of injection to the Peyer's patches was not determined and is not obvious. The authors suggested that the same agents might alter the migratory route taken by skin-residing dendritic cells subsequent to their antigen-induced maturation, however no experiments to test this hypothesis were mentioned.

WO 99/62537 suggests the use of agents that antagonize the dendritic cell membrane proteins, p-glycoprotein (MDR-1) and tissue factor, as a means to inhibit dendritic cell migration in pathologic conditions such as asthma, allergy, inflammation and graft rejection. MDR-1 is the multidrug efflux transporter that can render tumors resistant to chemotherapy. MDR-1 and tissue factor were found to be involved, in an unknown way, in the transendothelial migration of dendritic cells (Randolph et al. 1998 *Proc. Nat'l. Acad. Sci.* 95:6924–6929; Muller and Randolph 1999 *J. Leukoc. Biol.* 66:698–704). Transendothelial migration refers to passage of a cell across vascular endothelium and, in this case, entry into the lumen of afferent lymphatic vessels. Antagonists of MDR-1 were shown to diminish a) the transendothelial migration of dendritic cells in vitro, b) their egress from skin explants ex vivo (Randolph et al. 1998 *Proc. Nat'l. Acad. Sci.* 95:6924–6929), and c) the accumulation of immigrant Langerhans cells in the draining lymph node following contact sensitization in vivo (WO 99/62537). Therefore, the potential of such antagonists to suppress an immune response is supported.

WO 99/62537 further suggests the use of agonists of MDR-1 and tissue factor as adjuvants to be admixed with an antigen used for vaccination. The rationale is that this might "enhance" or "increase" dendritic cell migration. However, no evidence was provided that treatment with an agonist of MDR-1 or tissue factor has this effect. We have been unable to find any published indication that an experiment designed to test this hypothesis has been done. If a cell is able to cross vascular endothelium using some minimal number of surface proteins, artificially increasing the number of those proteins beyond the required minimum may have no effect. Therefore, it remains unknown whether increasing the expression or function of these receptors will increase the migration of dendritic cells. Moreover, no suggestions were made in WO 99/62537 that MDR-1 or tissue factor agonists would "induce migration", "initiate migration", or "mobilize" immature dendritic cells from their non-lymphoid tissue of residence, merely that such agonists might "increase . . . ", "enhance . . . ", or "modulate the migration" of dendritic cells.

U.S. Pat. No. 5,980,898 to Glenn et al., describes a patch for transcutaneous [topical] induction of an immune response, wherein an antigen is combined with an adjuvant such as ADP-ribosylating exotoxin; specifically, cholera toxin, *E.coli* heat-labile enterotoxin, or pertussis toxin. Topical application of an antigen combined with one of these adjuvants resulted in antibody responses to both the antigen and the adjuvant, while the antigen alone was not immunogenic. The antigens and toxins used in this procedure are large proteins (60,000–86,000 Da). The mechanism by which they reach epidermal Langerhans cells after topical application is not obvious, given that the stratum corneum is resistant to passive transport of large (>500 Da) or hydrophilic molecules (reviewed in Naik et al. 2000 *Pharm. Sci. and Technol. Today* 3:318–326). The only evidence presented for the possible involvement of Langerhans cells in this immunogenic effect was an apparent increase in the expression of MHC class II molecules on Langerhans cells and an apparent reduction in their number, found in epidermal sheets by immunofluorescence microscopy, 24 hours after epicutaneous application of cholera toxin.

An reduction in the apparent frequency of Langerhans cells in excised epidermal sheets is not necessarily evidence that antigen-bearing Langerhans cells have been induced to migrate to a lymph node. Some treatments are well known to diminish the detectable frequency of Langerhans cells in the epidermis while having the opposite effect on immunity; that is, they result in immunosuppression. Two such examples are UVB irradiation of the skin (Meunier 1999 *Eur. J. Dermatol.* 9:269–275) and topical application of dexamethasone or clobetasol propionate, both potent immunosuppressive glucocorticoid drugs (Furue and Katz 1989 *J. Invest. Dermatol.* 92:342–347; Nakamura et al. 1999 *J. Invest. Dermatol.* 4:169–172). Thus, a reduction in detectable Langerhans cells in epidermal sheets does not confirm the induction of their maturation and migration to draining lymph nodes, nor is it definitive of a procedure that induces immunity. Glenn et al. Stated recently that "the role of LCs [Langerhans cells] in TCI [transcutaneous immunization] remains to be determined" (Glenn et al. 2000 *Nature Med.* 6:1403–1406).

Another method of topical immunization involves application of naked DNA to normal mouse skin (Fan et al. 1999 *Nature Biotech.* 17:870–872) and has some features in common with the preceding transcutaneous method of Glenn et al. That is, the topically applied DNA is also large and hydrophilic. However, the DNA was found to gain entry via hair follicles in the skin. The immune response induced by the topically applied naked DNA was primarily antibody, with little detectable T cell proliferative response to the encoded antigen. Antibody production in the absence of significant antigen-specific T cell proliferation in lymph node cells is characteristic of the response induced by low doses of soluble protein antigens in certain mouse strains (Guery et al. 1996 *J. Exp. Med.* 183:485–497). In susceptible mouse strains, Th1 cells are tolerized to the antigen while Th2 cells are induced to secrete Il-4; in other strains, antigen-specific unresponsiveness is induced in both $CD4^+$ T helper cell subsets. This type of response, induced by low doses of soluble proteins and referred to as low-zone tolerance (In Immunobiology, 4th edition 1999 Janeway, C. A., Travers, P., Walport, M., and J. D. Capra, eds. Garland Publishing, New York, N.Y. p. 37), can result in non-protective immunity and is often associated with chronic infections. Moreover, a topical immunization procedure that depends on the antigen gaining entry via hair follicles is likely to be less effective in humans than in mice, because the density of hair follicles in mouse skin is about 10 times greater than the density of hair follicles in human skin.

One topically applied compound, imiquimod, has been shown to enhance the migration of epidermal Langerhans cells to draining lymph nodes (Suzuki et al. 2000 *J. Invest. Dermatol.* 114:135–141). When mouse skin was pre-treated for 3 days with imiquimod prior to the application of a contact sensitizing antigen, more Langerhans cells were found in the draining lymph node than in mice receiving the contact sensitizer alone. However, none of the patents describing the practical applications of imiquimod, e.g., U.S. Pat. Nos. 4,689,338, 5,750,495, 6,039,969, 6,083,505, and WO 00/47719, teach use of this compound to induce the migration and maturation of immature dendritic cells in vivo.

While the location, frequency and functional potential of Langerhans cells make them attractive targets for vaccine delivery, a localized injection of antigen would probably reach only a few nearby Langerhans cells or the occasional wandering dendritic cell. The exposure of Langerhans cells to antigens that are not inherently pro-inflammatory would probably be insufficient to induce functionally significant migration and maturation of the cells. Accordingly, the common practice of administering vaccines by sub-cutaneous or intramuscular injection, or 'gene gun' delivery, would fail to induce strong protective immunity to vaccines that are not inherently pro-inflammatory, due to their failure to cause adequate migration and maturation of antigen-bearing dendritic cells.

In related U.S. patent application Ser. No. 09/176,044, which is incorporated herein in its entirety by reference thereto, Cowing disclosed a vaccination procedure in which an antigen is administered topically to the skin or mucous membranes, and transported across the stratum corneum with passive penetration enhancers or active transport methods, for uptake by Langerhans cells in the epidermal layer of the skin or mucous membranes. The administration of the antigen was accompanied by topical application of an effective inducer of Langerhans cell migration, delivered to the same site. Effective means for topical induction of Langerhans cell migration were demonstrated to include low frequency ultrasound, and one or more members of certain classes of small organic compounds found to have the capacity to induce Langerhans cell migration to draining lymph nodes.

While the parent application concerned a topical method for transporting antigens across the stratum corneum to the immature Langerhans cells, in conjunction with an effective means to induce Langerhans cell maturation and migration, the present invention teaches and provides evidence that the application of an effective inducer of Langerhans cell migration is itself a means to induce these cells to capture antigen(s) delivered elsewhere or by other routes, and that might otherwise have little or no immunogenicity. Thus, the effective induction of immature dendritic cell migration and maturation constitutes a potent adjuvant, that can be delivered independently of and separately from delivery of the antigen.

In the present application, we provide support for our hypothesis that an injection of a protein or peptide antigen results in few if any antigen-bearing dendritic cells reaching the draining lymph node, and disclose the surprising discovery that effective topical induction of immature dendritic cell (Langerhans cell) migration can render an otherwise non-immunogenic administration of antigen into a potent immunogenic stimulus. We show that this can be accomplished even when the antigen is administered independently of the migration inducer and via a different route, to a different anatomical site. Thus, the effective induction of dendritic cell migration per se can be used as an "immunologic adjuvant" to achieve remarkably high levels of antigen-presenting dendritic cells in secondary lymphoid organs.

Fluorescein isothiocyanate (FITC) has been used extensively by the inventor and others, to characterize Langerhans cell migration. FITC is a small (389 Da) non-peptide, largely lipophilic molecule, capable of crossing the stratum corneum. The antigenicity of FITC is due to the reactivity of its isothiocyanate group (—N=C=S) with free amino groups, permitting it to be covalently bound to proteins and/or peptides. C57BL/6 mice received the following treatments: 1) none; 2) shaving of the abdominal skin only; or shaving of the abdominal skin followed by either 3) topical administration of FITC in acetone; 4) topical administration of FITC in acetone and olive oil; 5) topical administration of FITC in acetone and DMSO diluted in phosphate buffered saline (PBS); or 6) topical administration of FITC in acetone and dibutyl phthalate. The draining inguinal lymph nodes were then examined for immigrant dendritic cells by immunofluorescent flow cytometry each day thereafter. Migratory Langerhans cells were identified by the presence of FITC and co-expression of high MHC class II molecules or by co-expression of the DEC 205 ligand for the monoclonal antibody, NLDC-145. Dendritic cell residents of the lymph nodes could be differentiated by their high expression of MHC class II molecules but lack of FITC, or by their lack of FITC but co-expression of the ligand for the dendritic cell-specific monoclonal antibody, 33D1. The uptake of FITC and the Langerhans cell response to migratory signals were observable in the draining lymph node as early as six hours after topical administration. However, 48–72 hours was required for maximal immigration of FITC-bearing Langerhans cells into the lymph node. FIG. 1 illustrates the effect of various treatment regimens on the total and FITC+ dendritic cells 2 days after treatment. In animals administered FITC in acetone, there was no enhancement in FITC+ Langerhans cell number induced by olive oil or dimethylsulfoxide (DMSO). The addition of dibutyl phthalate had a striking effect on both FITC+ and total dendritic cell migration into the lymph node. Thus, dibutyl phthalate was a very potent migration inducer.

Figure 2:
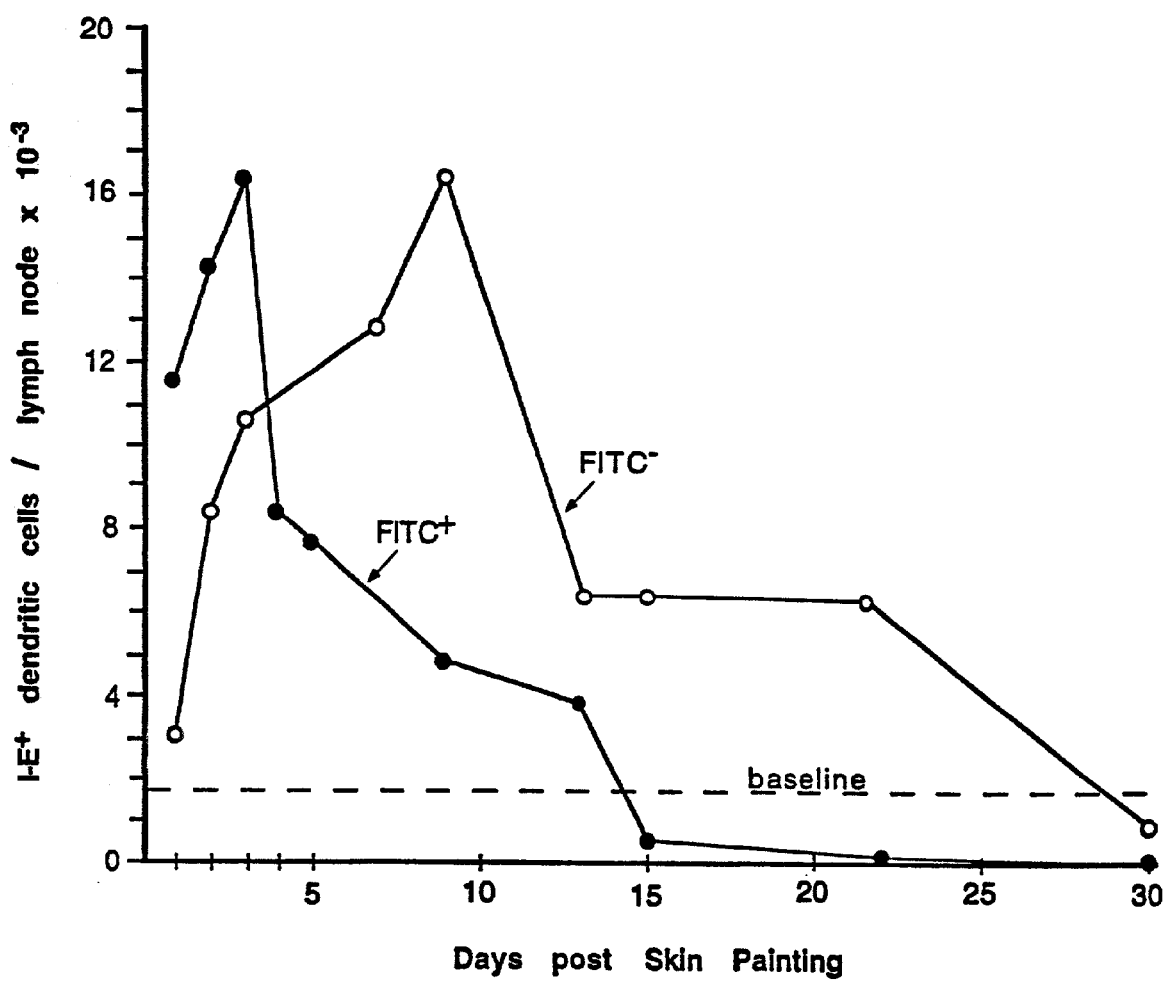
FIG. 2 shows the kinetics of dendritic cell migration to the draining lymph node in response to topical FITC in acetone and dibutyl phthalate.

In mice treated with FITC in acetone and dibutyl phthalate, the kinetics of Langerhans cell migration is shown in FIG. 2. High numbers of FITC+ Langerhans cells were present in the lymph node by 12 hours, and the peak frequency of immigrant FITC+ Langerhans cells occurred about 2 to 3 days following topical administration. Note however, that in addition to inducing the migration of FITC+ Langerhans cells, the number of unlabeled (FITC-negative) dendritic cells was also markedly enhanced, reaching peak levels 9–10 days following treatment.

Figure 3:
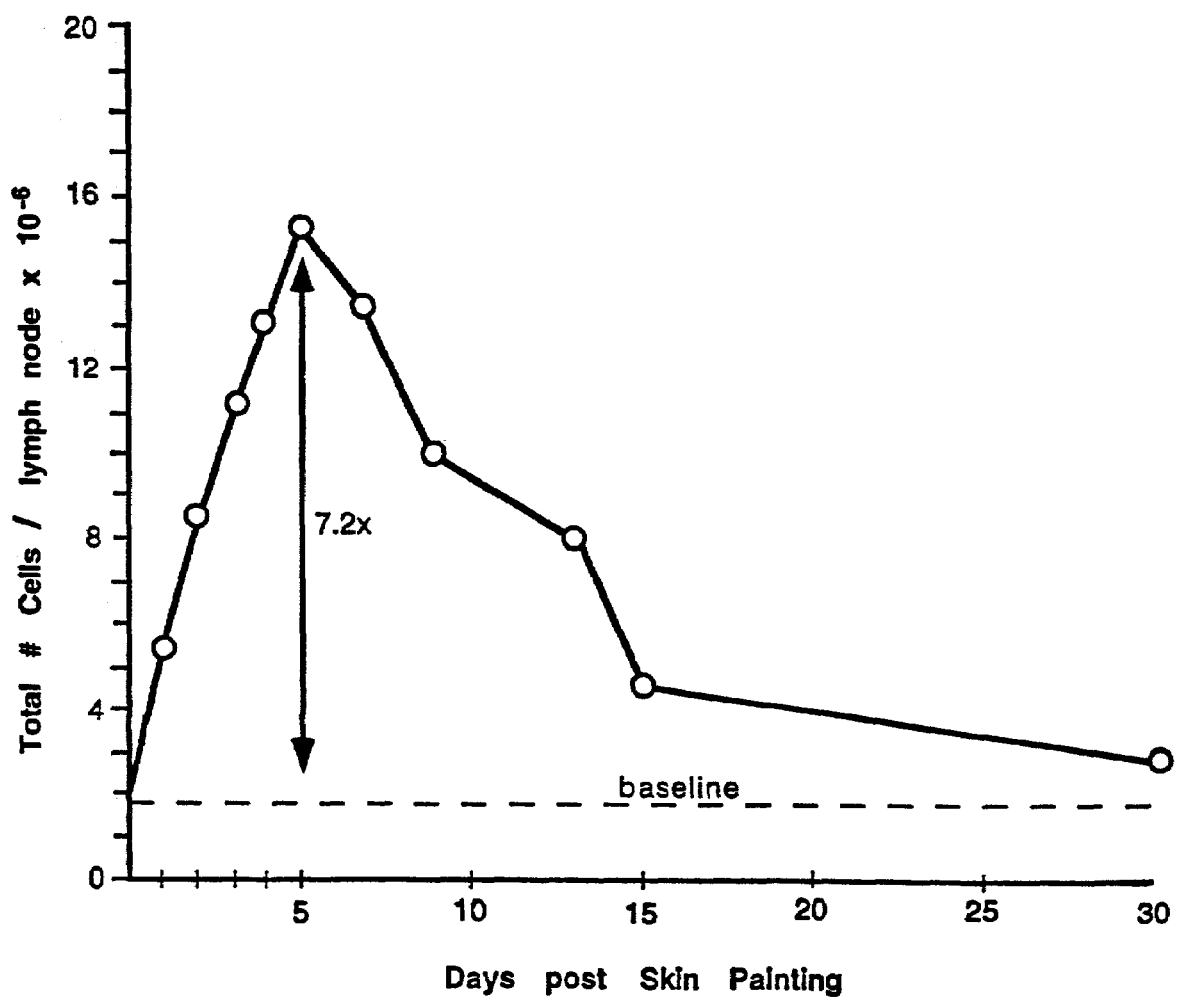
FIG. 3 shows the effect of topical administration of FITC in acetone and dibutyl phthalate on total lymph node cell number.

Total lymph node cells in response to the topical administration is shown in FIG. 3. Five days after topical administration of FITC in acetone and dibutyl phthalate, the lymph node cell population had increased by approximately 7.2 fold over baseline levels. These results indicate that antigen (FITC) in acetone and dibutyl phthalate not only stimulated antigen+ Langerhans cell migration, but also resulted in a dramatic increase in the total number of dendritic cells in the draining lymph node, as well as an increase in the total cellularity of the lymph node. Immunofluorescent flow cytometry also revealed the development of activated T and B cells in the draining lymph node.

Induction of Langerhans Cell Migration can Promote Tumor-Specific Immunity

The tumor cell, E.G7-OVA, is the C57BL/6 EL4 thymoma transfected with the complete gene for chicken ovalbumin (OVA). The transfected cell line expresses OVA protein, which is also processed naturally by E.G7-OVA cells into an eight amino acid peptide, $OVA_{257-264}$, with the sequence SIINFEKL. This peptide becomes expressed on the plasma membrane in a complex with the MHC class I molecule $K^b$ as $K^b$:SIINFEKL, where it has been demonstrated to function as a tumor-associated peptide antigen for CD8+ cytotoxic T cells (CTL) both in vitro and in vivo (Celluzzi et al. 1996 *J. Exp. Med.* 183:283). Based on the positive results using FITC, the inventors followed a similar protocol in an attempt to induce immunity to the E.G7-OVA tumor by topical administration of the well-characterized, synthetic SIINFEKL tumor-associated peptide.

Figure 4:
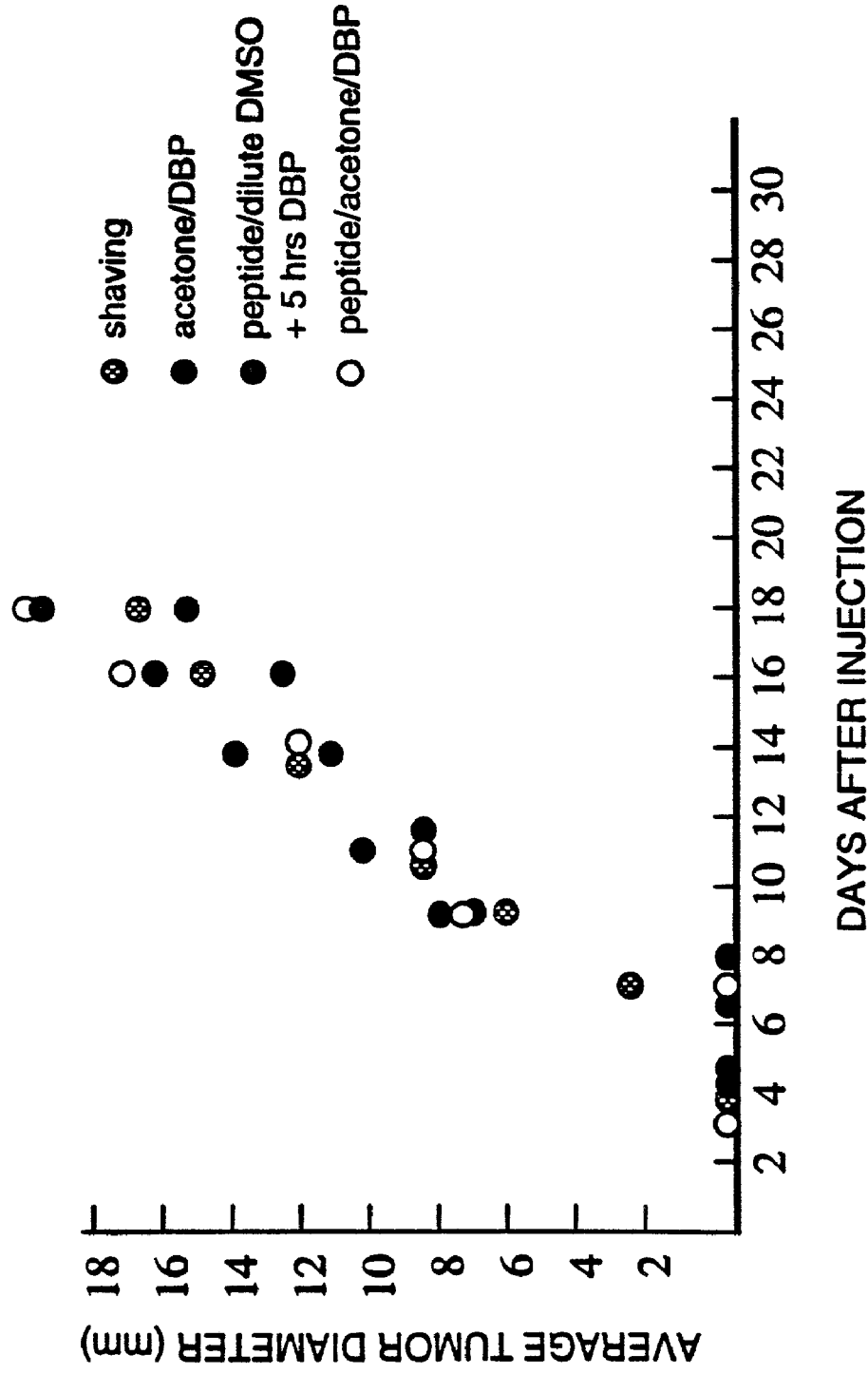
FIG. 4 shows poor inhibition of E.G7-OVA tumor growth by cutaneous topical administration of the tumor peptide SIINFEKL in acetone and dibutyl phthalate.

C57BL/6 mice were treated as follows: 1) shaving alone; 2) topical administration of acetone and dibutyl phthalate; 3) topical administration of SIINFEKL (240 µg/ml) in DMSO diluted in PBS, followed in 5 hours by acetone and dibutyl phthalate; and 4) topical administration of SIINFEKL (240 µg/ml) in acetone and dibutyl phthalate. All mice were subsequently injected subcutaneously with $5\times10^5$ E.G7-OVA cells (5-times the minimal tumorogenic dose). Tumor-specific immunity was monitored by measuring the size of the developing tumor. The results shown in FIG. 4, indicate that none of the treatment protocols were effective in inhibiting tumor cell growth. Since it was known from the FITC experiments that dibutyl phthalate was a potent Langerhans cell migration inducer, and that SIINFEKL was readily incorporated into the MHC class I molecule $K^b$ where it can activate CD8+ CTLs (Celluzzi et al. 1996 *J. Exp. Med.* 183:283), it was concluded that the SIINFEKL peptide did not cross the stratum corneum in sufficient concentration to induce a primary immune response.

Similarly, when an aqueous solution of a SIINFEKL peptide or OVA protein antigen was applied to the skin along with topical application of the migration inducer, DBP and acetone, no detectable antigen-bearing (i.e., $K^b$:SIINFEKL positive) dendritic cells appeared in the draining lymph node (data not shown).

Figure 5:
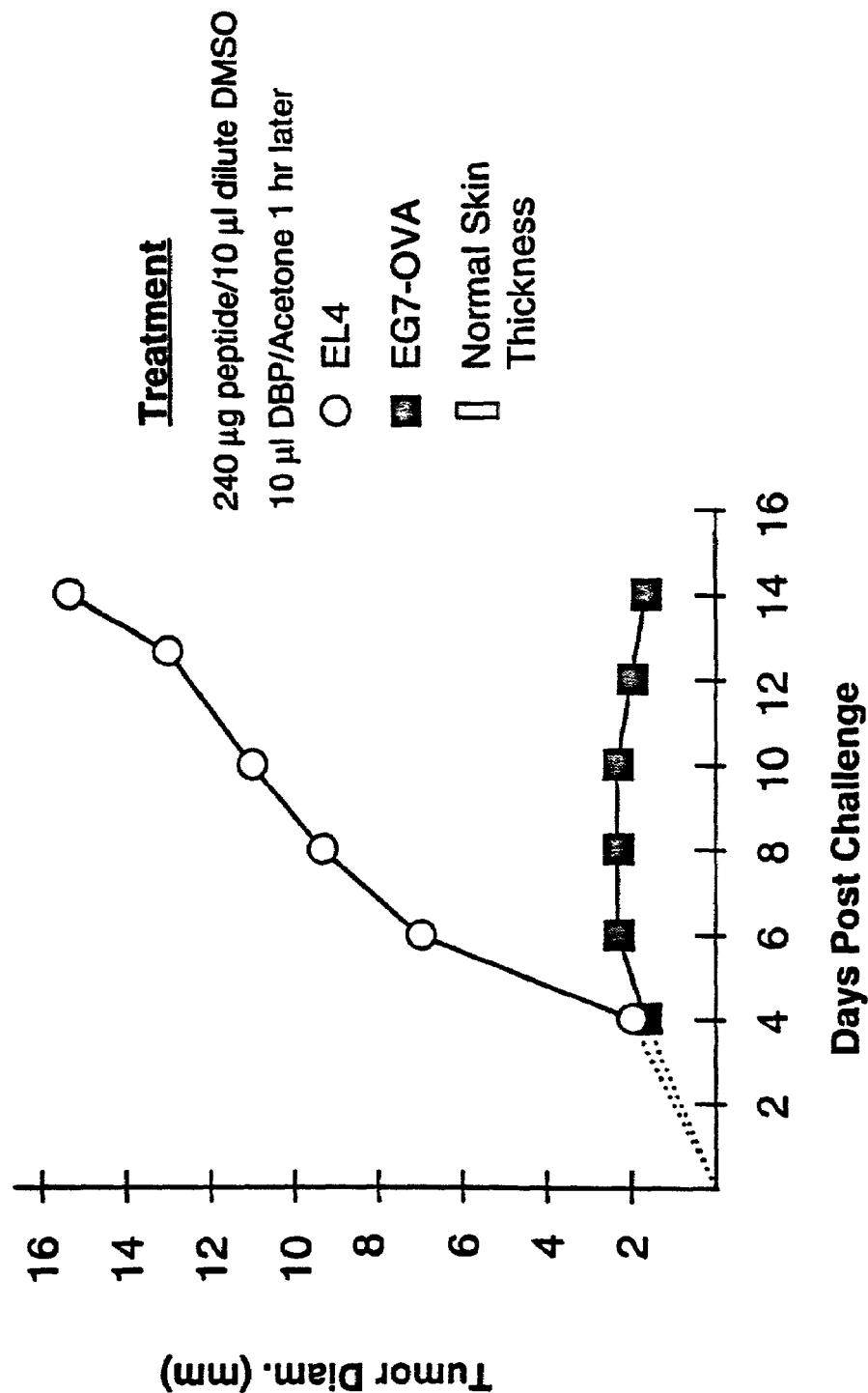
FIG. 5 illustrates the induction of E.G7-OVA tumor-specific immunity by intravaginal application of SIINFEKL in acetone and dibutyl phthalate.

Since it was postulated that topical administration of SIINFEKL in acetone and dibutyl phthalate had failed to confer tumor-specific immunity because the peptide did not penetrate the stratum corneum efficiently, the same topical vaccine was applied intravaginally. The mucous membranes lack the tough barrier posed by the stratum corneum of the skin. The results shown in FIG. 5 suggested that protection against the tumor was induced by the application of SIINFEKL in acetone and dibutyl phthalate to the vaginal epithelium. The EL4 parent tumor cell line, lacking chicken ovalbumin, was used as a negative control; no immunity against the EL4 tumor cells was seen. Thus, the inventors' hypothesis regarding penetration of the stratum corneum was confirmed; the SIINFEKL peptide was not effectively reaching the immature dendritic cells, known as Langerhans cells, underlying the stratum corneum.

Figure 6:
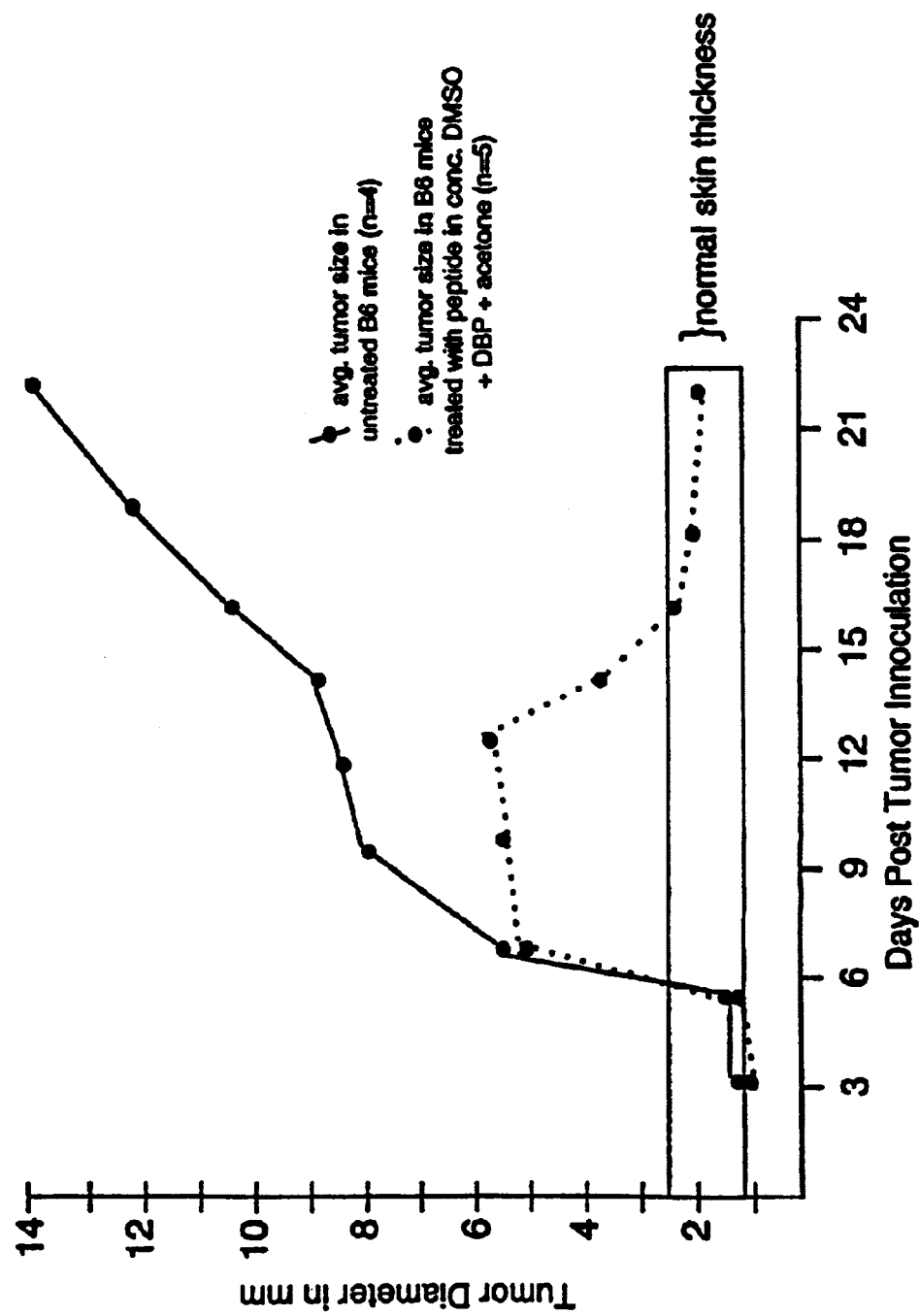
FIG. 6 shows inhibition of E.G7-OVA tumor growth by cutaneous topical administration of SIINFEKL in concentrated DMSO, followed by dibutyl phthalate in acetone.

To enhance the effectiveness of cutaneous topical administration of peptide, SIINFEKL was dissolved in DMSO and applied to the skin without further dilution. Dibutyl phthalate in a 50:50 mixture with acetone was applied to the same site 5 hr later. All mice were subsequently injected subcutaneously with $5\times10^5$ E.G7-OVA cells. The results shown in FIG. 6 indicate that the peptide in concentrated DMSO was apparently able to traverse the stratum corneum, effectively gaining access to the epidermal Langerhans cells. Tumor growth was suppressed after 6 to 9 days, and even the established tumors were diminished by 16 days post-inoculation. Thus, the tumor-specific peptide, SIINFEKL, in concentrated DMSO, penetrated the stratum corneum in sufficient concentration to be incorporated into the MHC class I molecule $K^b$ on epidermal Langerhans cells, and in the presence of the migration inducer, dibutyl phthalate, was effectively presented to CD8+ CTLs in the draining lymph nodes.

Antigen Source

The antigen or epitope(s) thereof in accordance with the present invention may be small peptides, proteins, or non-peptide immunogenic compounds. Where the antigen is introduced into the mammal by parenteral and other non-topical routes, the size of the antigen is not limiting for the disclosed immunization method. Similarly, where the antigen is introduced into the mammal by a infecting cell (virus, bacteria, parasite, etc.), the antigen characteristics are not limiting. Likewise, where immunization involves transfer of a nucleic acid that encodes an antigenic peptide or protein, the characteristics of the antigen per se does not limit the delivery route. In accordance with one mode of the present invention, the antigen may be endogenous, e.g., a tumor antigen.

However, where topical delivery of the antigen is employed, then small peptide antigens are preferred, although not essential, because it is easier to get smaller peptides (about 8–20 amino acid residues) across the stratum corneum and into the epidermis than larger proteins. Furthermore, properly sized peptides, like SIINFEKL, are likely to bind directly to MHC molecules on the Langerhans cell surface through the process of peptide exchange, in which the exogenously added peptides displace those endogenous peptides that have a lower affinity for the peptide binding groove of the MHC class I or II molecules. Characteristics of peptides suitable for direct association with class I or II MHC molecules have been studied extensively. Thus, those skilled in the art would be able to predict, based upon peptide structure, sequences likely to associate with a given MHC allelic product. Peptides which bind effectively to class I MHC molecules are generally comprised of about 8–10 amino acid residues, whereas peptides which associate preferentially with the class II MHC molecules are ultimately about 13–17 amino acid residues in length. Indeed, several antigenic peptides capable of interacting directly with MHC molecules are known and can be synthesized by standard techniques.

Alternatively, while specific tumor-associated antigens have been identified for many human tumors, the relevant peptides are often unknown. Nonetheless, crude acid-eluted tumor peptides can be prepared quickly and easily and have been shown to be effective inducers of tumor-specific immunity when associated with dendritic cells (Zitvogel et al. 1996 *J. Exp. Med.* 183:87–97). Thus, both known, homogeneous preparations of synthetic peptides, as well as unknown mixtures of extracted peptides, may be suitable for use in the present invention. The choice and preparation of suitable peptide antigens is well within the skill of those in the art.

Non-peptide immunogenic compounds capable of induction of specific immunity are also contemplated as potential antigens in accordance with the present invention. As an experimental example, small non-peptide haptens, such as FITC, may covalently bind to peptides or proteins after crossing the stratum corneum, thereby gaining access to standard antigen presentation pathways, through association with an MHC or antigen-presenting MHC-like molecule, e.g., CD1. The antigenicity of FITC is due to the reactivity of its isothiocyanate group (—N=C=S) with free amino groups, permitting it to be covalently incorporated within proteins and/or peptides. Other non-peptide antigenic moieties that occur naturally or are introduced into tumor cells, pathogens, parasites, allergens, etc., may be used in practicing the vaccination methods of the present invention.

It should be noted that choice of the source of antigen is not critical to the invention, which is a general method for enhancing antigen-specific, adaptive immunity. However, the specific immune response obtained will, of course, depend on the particular antigen employed. It is the manner of the induction of immature dendritic cell migration and maturation and subsequent antigen presentation by MHC and MHC-like-dependent pathways, which individually or in combination, exemplify the features of the disclosed invention. The fact that no limitations are placed on the selection of antigens from a wide variety of sources is consistent with use of the basic methods for inducing antigen-specific immunity or tolerance to many antigens. Thus, the choice of a particular antigen and its source will depend on the application and is within the ordinary skill of those in the field of immunology.

Penetration of the Stratum Corneum

The outer layer of the skin is designed to resist entry of foreign materials into the body. Because it is formed of densely packed layers of keratinocyte cell membranes and keratin fibrils, the stratum corneum is impermeable to most molecules of molecular mass greater than 500 Da, particularly those of a hydrophilic nature. Consequently, only a few drugs are administered transdermally. Such molecules are typically small and lipophilic. The transdermal delivery of peptides is ill-favored because of their hydrophilicity and generally high molecular mass. Numerous studies document the great difficulty in getting peptides through the stratum corneum (for review, see Steinstrasser and Merkle 1995 *Pharm. Acta. Helv.* 70:3–24). Among the approaches which have yielded some success in enhancing peptide penetration are included lipophilic vehicles, low frequency ultrasound, electroporation, iontophoresis, and intraepidermal delivery. These are considered below.

Lipophilic Solvents—Lipophilic solvents like acetone, azone, and dimethylsulfoxide (DMSO) are known to penetrate the stratum corneum. As discussed above, the inventor has found that small peptides, like SIINFEKL, dissolved in DMSO cross the stratum corneum and enter the lower strata of the epidermis. Thus, the present disclosure with respect to antigen penetration enhancers, encompasses a variety of lipophilic solvents, including DMSO, and symmetrical or unsymmetrical sulfide and sulfoxides where the alkyl group contains 1 to 16 carbon atoms, as well as liposomes.

Where lipophilic penetrants, such as DMSO, are employed in the present invention to enhance peptide penetration, such solvents may be administered neat or diluted with other solutions, such as PBS. Ratios of mixtures may range from about 1:9 to about 9:1 (penetrant to diluant). Preferably, the penetration enhancer is undiluted.

Low Frequency Ultrasound—Mitragotri et al. reported that even large protein molecules, such as insulin (6,000 Da), IFN-γ (17,000 Da), and erythropoietin (48,000 Da) could be coaxed into crossing the stratum corneum using low frequency ultrasound (Mitragotri et al. 1995 *Science* 269: 850–853; incorporated herein by reference). Ultrasound works on skin by non-thermal, cavitational effects, creating micro-bubbles that expand and contract in the stratum corneum, resulting in a transient increase in permeability. Cavitation increases as the frequency of ultrasound decreases and is optimal at lower frequency sound waves than that used for diagnostic imaging (2–12 Mhz).

Electroporation—Vanbever et al. disclosed that about 10% of the small (267 Da) molecule, metoprolol, could be transported across the skin during 4 hr after 5 single 450 V pulses (Vanbever et al. 1994 *Pharm. Res.* 11:1000–1003; incorporated herein by reference). Electroporation has been used extensively for permeabilization of cell membranes for the purpose of getting DNA into cells. Transdermal transport of peptides may be accomplished by localized exposure of the skin to high intensity electric field pulses, which may create transient aqueous pores in the lipid bilayers.

Iontophoresis—Bodde et al. found that only about 0.4% per hour of vassopressin (1,084 Da) crossed the stratum corneum (Bodde et al. 1990 *Biochem. Soc. Trans.* 17:943–945; incorporated herein by reference). Iontophoresis involves exposing the skin to low intensity current. Polar molecules move in response to the current, and transport is believed to occur via glands or hair follicles which project through the epidermis down into the dermis. This method is encompassed within the present invention.

Intradermal Delivery—Certainly, the stratum corneum can be penetrated using sharp instruments. Thus, intraepidermal or intradermal injections using traditional beveled needles and syringes is possible. Similarly, introduction of the antigenic agents into the epidermis using pronged instruments, like those used for administration of the tine test, is also possible. Antigens can also be propelled into the epidermis by high-pressure fluids or gases, such as those used in needle-free injection systems. Such invasive physical methods may solve the penetration problem and may even provide concomitant migratory signals to the Langerhans cells.

Induction of Langerhans Cell Migration

While effectively bringing antigens into contact with the Langerhans cells in the epidermis may be necessary for induction of the immune response, it is not by itself sufficient to induce the strong antigen-specific immunity desired for a vaccination procedure. Although the phenomenon of Langerhans cell migration from the epidermis to the lymph nodes has been known for many years, the complex regulatory pathways which control Langerhans cell migration and maturation in vivo are not fully understood. Moreover, there are apparently a number of commonly held misconceptions regarding Langerhans cell migration. For example, some investigators believe that the spontaneous and/or continuous migration of Langerhans cells is sufficient for induction of antigen-specific immunity (see e.g., Matsuno et al. 1990 *J. Exp. Med.* 183:1865). Others in the field have suggested that contact sensitizing antigens are capable of inducing Langerhans cell migration by themselves, therefore a separate induction stimulus may not be needed for any antigens (see e.g., Udey 1997 *Clin. Exp. Immunol.* 107:6). Accordingly, scientists using FITC in acetone and dibutyl phthalate to study Langerhans cell migration have suggested that it is the antigen (FITC) which induces migration (see e.g., Wang et al. 1996 *Immunol.* 88:284).

At present, inquiry into the regulation of Langerhans cell migration focuses primarily on the production of cytokines and chemokines, which appear to modulate Langerhans cell migration and maturation. For instance, granulocyte-macrophage colony-stimulating factor (GM-CSF) and interleukin-1α (IL-1α) may mediate in vitro maturation (Larregina et al. 1996 *Immunology* 87:317–325). Tumor necrosis factor-α (TNF-α) is involved in Langerhans cell migration (Banchereau and Steinman 1998 *Nature* 392:245). Other factors implicated in the control of various aspects of Langerhans cell maturation and/or migration include MIP-1α, IL-4, G-protein-coupled receptors for the calcitonin-gene related peptide, C5a and other chemokines (Banchereau and Steinman 1998 Nature 392:245). Thus, while many possible signals and signaling pathways have been identified, the regulatory scheme remains obscure.

In general, the types of compounds useful in the present invention are often diesters or diamides of an acid anhydride or dicarboxylic compound. The esters in this compound are typically formed of the dicarboxylic compound esterified with two groups selected independently from a 1 to 16 carbon alkyl moiety and/or aryl moiety. The aryl moieties are preferably substituted or unsubstituted benzyl or phenyl moieties. In one embodiment, both ester moieties are identical. In another embodiment, the ester moieties are different. These migration inducers generally have a molecular weight of less than or equal to 500 daltons and an oil-water partition coefficient of between about 10 and $10^6$.

More particularly, the chemical inducers of Langerhans cell (or immature dendritic cell) migration of the present invention comprise a compound having formula (1) or formula (2) or formula (3):

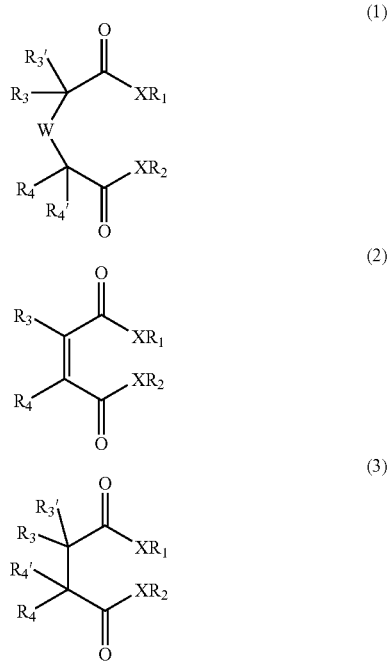

wherein $R_1$ and $R_2$ are independently alkyl side chains containing 1 to 16 carbon atoms, $C_1$ to $C_{16}$ substituted alkyl, $C_3$ to $C_{10}$ cycloalkyl, $C_3$ to $C_{10}$ substituted cycloalkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl; and wherein $R_3$, $R_3'$, $R_4$ and $R_4'$ are selected independently from the group consisting of hydrogen atom, hydroxy group, halogeno group, alkyl side chains containing 1 to 16 carbon atoms, $C_1$ to $C_{16}$ substituted alkyl, $C_3$ to $C_{10}$ cycloalkyl, $C_3$ to $C_{10}$ substituted cycloalkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_7$ to $C_{16}$ phenylalkyl, $C_7$ to $C_{16}$ substituted phenylalkyl, phenyl, substituted phenyl, naphthyl and substituted naphthyl. In one variation, $R_1$ and $R_2$ groups may be identical $C_1$ to $C_6$ alkyl moieties. Preferably, $R_1$ and $R_2$ are $(CH_2)_3$—$CH_3$. X is an oxygen (O), or a nitrogen atom (N).

W is a saturated or unsaturated chain consisting of $C_1$–$C_{10}$ alkyl, $C_1$–$C_{10}$ substituted alkyl, $C_7$–$C_{10}$ phenylalkyl, $C_7$–$C_{16}$ substituted phenylalkyl, phenyl, substituted phenyl, naphthyl, substituted napthyl, $C_3$–$C_7$ cycloalkyl and $C_3$–$C_7$ substituted cycloalkyl group. Each terminus of the chain is bonded to the carbon $C(R_3R_3')$ and $C(R_4R_4')$. The chain w may contain one or more heteroatoms selected from the group consisting of nitrogen, sulfur, and oxygen in combination or independently.

In one variation to the compound, X is oxygen (O) and $R_3$ and $R_4$ are linked to form a ring structure which, including the W chain, comprises saturated or unsaturated $C_3$ to $C_{10}$ cycloalkyl, $C_3$ to $C_{10}$ substituted cycloalkyl, $C_7$ to $C_{16}$ phenylalkyl, $C_7$ to $C_{16}$ substituted phenylalkyl, phenyl, substituted phenyl, naphthyl or substituted naphthyl. Preferably, the ring structure is an aryl group. The ring may contain one or more heteroatoms selected from the group consisting of nitrogen, sulfur, and oxygen.

In another variation, the compound of the present invention may be a terpene.

In a preferred formulation, the immature dendritic cell migration inducer(s) are mixed with an organic solvent, such as acetone.

Specific compounds encompassed within the present invention for induction of Langerhans cell (immature dendritic cell) migration are provided below:

| Abbreviation | Compound |
|---|---|
| DBP | dibutyl phthalate |
| DBT | dibutyl-D-tartarate |
| DET | N,N-diethyl-toluamide |
| DBF | dibutylfumarate |
| DEHF | di(2-ethylhexyl)fumarate |
| DIOM | diisooctylmaleate |
| DEHM | di(ethylhexyl)maleate |
| DIOF | disooctylfumarate |
| BA | benzoic acid |
| C | camphor |
| BM | bihenylmaleate |
| DOP | dioctylphthalate |
| DBM | dibutylmaleate |
| DOM | dioctylmaleate |
| DBS | dibutylsuccinate |
| DOS | dioctylsuccinate |
| DNP | dinonylphthalate |
| DINP | diisononylphthalate |
| DMP | dimethylphthalate |
| DEP | diethylphthalate |
| DPP | dipropylphthalate |
| DPhP | diphenylphthalate |
| DBBP | dibenzylbutylphthalate |
| DMEP | diethylmethylphthalate |

Compounds which are useful as inducers of immature dendritic cell migration may be screened using the standard FITC methods described for the data presented in FIGS. 1—3. C57BL6 mice are shaved on their abdomens and painted with 100–200 μl of the test solution, containing 5 mg/ml FITC in a 50/50 (v/v) mixture of acetone and the migration inducer (e.g. dibutyl phthalate). After 2 days, the draining inguinal lymph nodes are removed and the total number of dendritic cells (both FITC+ and FITC−) is determined by flow cytometry and MHC class II immunofluorescence or other markers specific for dendritic cells.

Figure 7:
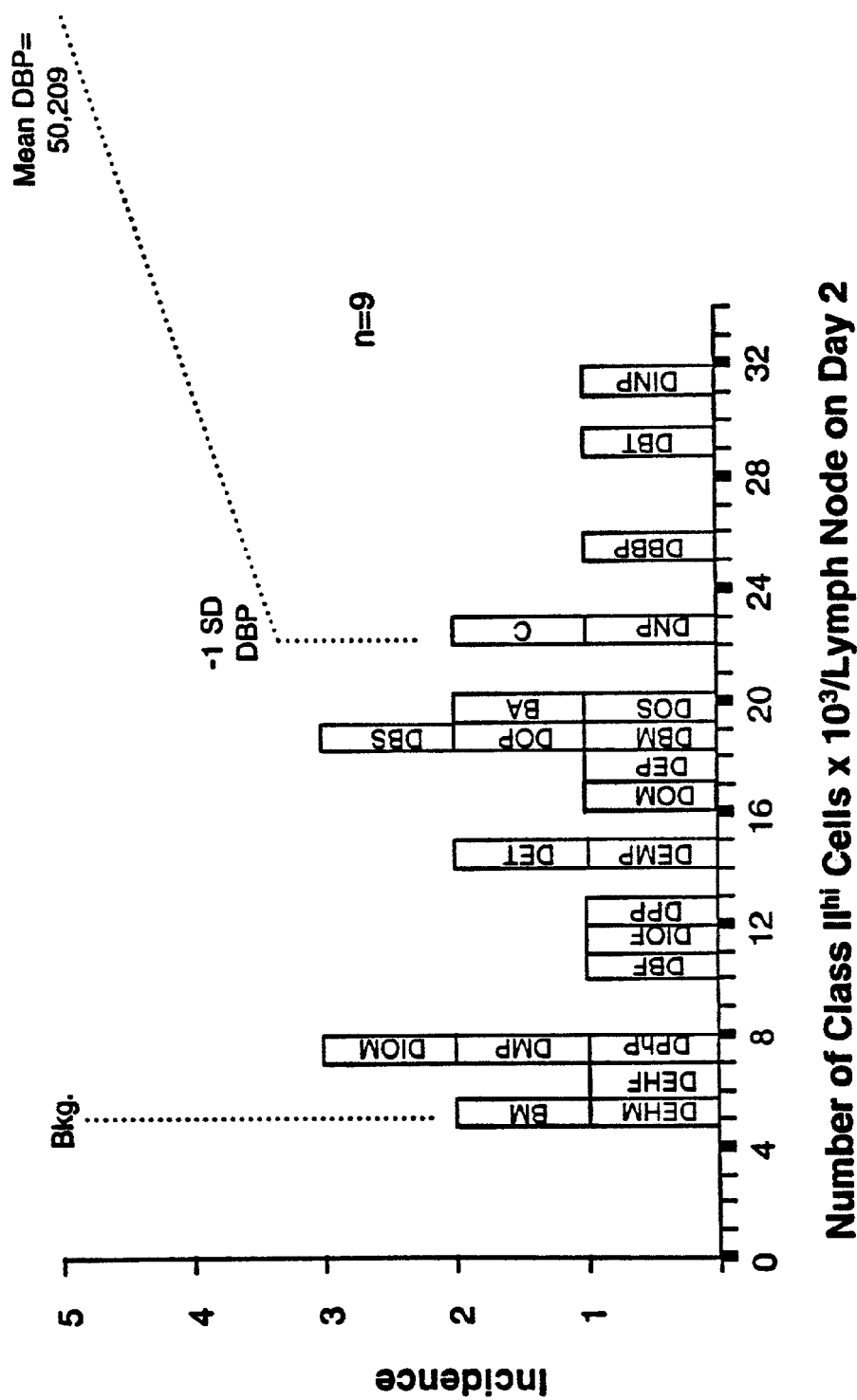
FIG. 7 shows the effect of various potential inducers of Langerhans cell migration in the FITC screening assay.

Test results are shown in FIG. 7. Total MHC class $II^{hi}$ cells were increased over background for most compounds tested. DNP, C, DBBP, DBT, and DINP induced migration that was within 1 standard deviation of the positive control, dibutyl phthalate (DBP).

Besides the chemical inducers of Langerhans cell (immature dendritic cell) migration, the inventor has found that low frequency ultrasound also exhibits positive results in the FITC migration screening procedure described above. Thus, in one embodiment of the present invention, low frequency ultrasound may be employed both as a penetrant and/or as an inducer of Langerhans cell migration.

The peptides/antigens used in accordance with the present invention may generally be applied topically in a dose range of approximately 1 µg/ml to about 100 mg/ml. Preferably, peptide antigens may be administered within the dose range of 1 mg/ml to 25 mg/ml. Topical administration to the skin may include from 0.01 to 1 ml/cm$^2$ application volumes, preferably about 0.05 to 0.5 ml/cm$^2$. Obviously, the larger the surface area that is treated the greater the number of Langerhans cells that will be induced to migrate to the draining lymph node. Routes of administration may be selected from any epidermal and/or mucous membrane sites including, the skin, intravaginal, rectal, aerosol delivery to the airways and lungs, and administration to the GI tract. Where chemical inducers of Langerhans cell migration are applicable, the chemical inducer may be given neat or mixed with an organic solvent, such as acetone, in a range of ratios from about 1:1000 to about 9:1 (inducer to solvent), preferably in a range of ratios from about 1:100 to about 7:3.

In some instances, it may be advantageous, merely to enhance Langerhans cell (immature dendritic cell) migration, without specifically administering any antigen. For example, where an individual has a skin cancer, such as melanoma or basal cell carcinoma, it may be useful in enhancing an immune response against the tumor to administer an inducer of Langerhans cell migration to sites surrounding the tumor, before surgery. Alternatively, topical administration may follow excision and subsequent chemotherapy and/or radiation.

The induction of Langerhans cell migration in accordance with the present invention can be described and determined by those of skill in the art with reference to the following general functional characteristics:

(1) The induction of Langerhans cell (immature dendritic cell) migration results in the appearance of antigen-bearing, mature dendritic cells in the draining lymphoid organ. The influx of antigen-bearing dendritic cells can range from about 2 to 1000 times the number of dendritic cells found in the unstimulated lymphoid organ, preferably from about 5 to 100 times the number of resident dendritic cells.

(2) The dendritic cells may be identified by markers characteristic of mature dendritic cells. In the mouse, these include: high expression of MHC class II molecules and other lineage markers such as DEC 205 and/or 33D1, expression of co-stimulatory molecules such as B7-1 (CD80) and B7-2 (CD86), expression of intercellular adhesion molecules such as ICAM-1 (CD 54) and LFA-3, and expression of other activation markers such as CD40 and CD44. Those of skill in the art will recognize human equivalents to the mouse markers where such equivalents are known.

(3) The antigen-bearing dendritic cells are detectable in the draining lymphoid organ approximately 6 to 12 hours after a single induction of maturation and migration, reach maximum numbers between 24 and 72 hours after induction, and subsequently diminish in number and become undetectable by 7 to 10 days after the initial induction.

(4) The initial influx of antigen-bearing dendritic cells is followed by an influx of antigen-free dendritic cells into the draining lymphoid organ that is detectable from approximately 24 hours up to one month after the initial induction. From 48 hours after the induction, it is necessary to exclude activated B cells from the dendritic cell detection system, this can be accomplished with the use of a B cell-specific marker such as CD19, or by use of an experimental animal lacking B cells.

(5) The antigen can be specifically detected on the immigrant dendritic cells by a variety of means, such as for example, the use of a fluorescent label, a colorimetric label, or a radiolabel, or with antibodies or other ligands specific for the peptide:MHC complex.

(6) An effective method could be identified by its ability to cause the local release of endogenous inducers of dendritic cell maturation and migration, such as but not limited to TNF-α and IL-1β, and to result in reduced membrane expression or function of the relevant non-lymphoid tissue-specific adhesion molecules, such as E-cadherin on epidermal Langerhans cells.

Quantitative Detection and Half-Life of Antigen-Specific Peptide:MHC Complexes on Primary Epidermal Langerhans Cells in vitro To evaluate the immunogenic potential of various vaccine formulations and delivery methods, an antigen system that permits quantitative determination of the number of specific peptide:MHC complexes expressed on the cell membrane was used. To date, the only direct way to quantitate antigenic epitopes expressed on living cells and recognized by T cells is with the use of monoclonal antibodies (mAbs) specific for individual peptide:MHC complexes. Chicken ovalbumin (OVA) is a 40 kDa protein that has been used for many years as a prototypic experimental antigen for immunologic studies. The $OVA_{257-264}$ peptide, SIINFEKL (963 Da), is processed and presented in the peptide-binding groove of the MHC class I molecule $K^b$. The mAb, 25-D1.16, has specificity for the SIINFEKL:$K^b$ complex (Porgador et al. 1997 *Immunity* 6:715–726).

Primary epidermal Langerhans cells were obtained from cultured explants of C57BL/6 dorsal ear skin according to the method of Ortner et al. (Ortner et al. 1996 *J. Immunol. Meth.* 193:71). Over a period of 72 hrs in culture, Langerhans cells mature and migrate out of the explant, dropping onto the bottom of the culture dish. These cells were harvested and incubated for 1.5 hrs at 37° C. with various concentrations of synthetic SIINFEKL peptide. The cells were then washed and stained with a FITC-conjugated anti-MHC class II (I-$A^b$) mAb, as well as with affinity purified and biotinylated 25-D1.16 followed by PE-avidin, and analyzed on a FACScan® flow cytometer. Non-specific binding of immunoglobulin proteins was blocked by pre-incubation and staining of the cells in a mixture of isotype control mAbs (rat IgG2a, rat IgG2b, mouse IgG1 and mouse IgG2a, each at 100–200 µg/ml) and the anti-Fc receptor mAb 2.4G2. Langerhans cells were identified by their characteristic light scatter properties (high forward, moderate side scatter) and exceptionally high levels of MHC class II expression, with the latter used to optimize the light scatter gate for each experiment. Dead cells were excluded from analysis by their uptake of 7AAD (7-amino-actinomycin D).

Figure 8:
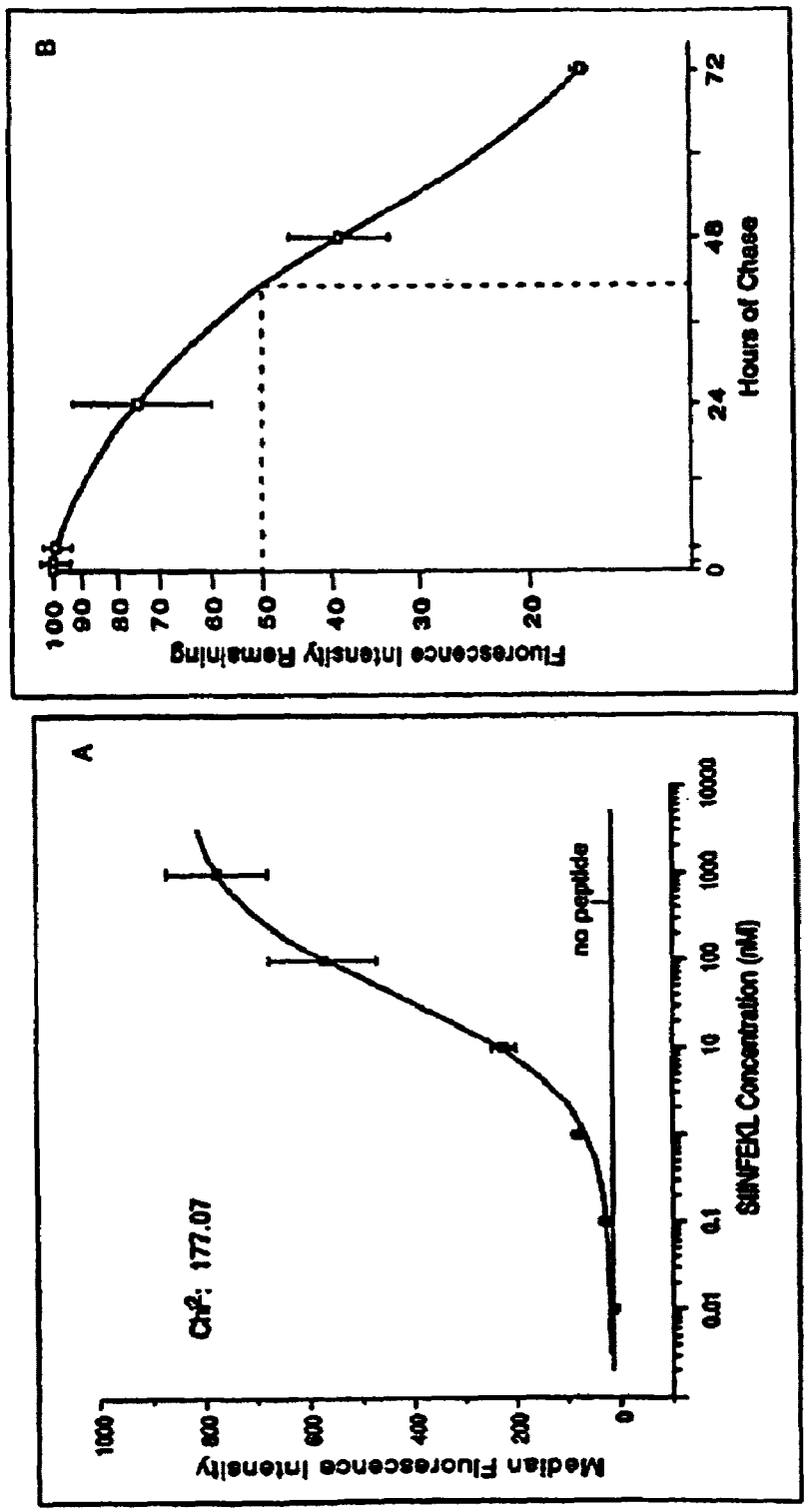
FIG. 8 shows the quantitative detection and half-life of specific peptide:MHC complexes on primary epidermal Langerhans cells after exposure to various concentrations of a peptide antigen in vitro.

FIG. 8A shows the median fluorescence intensity (arbitrary units) of Langerhans cells stained with 25-D1.16 after incubation with 0.01 nM to 10 µM SIINFEKL, as well as the median fluorescence intensity of an aliquot of the same cell population incubated in the absence of SIINFEKL (no peptide) but stained identically. Each data point represents the mean and S.E. of 3 to 5 independent experiments. These results demonstrate that SIINFEKL:$K^b$ complexes can be accurately and reproducibly measured on primary Langerhans cells after exposure to a wide range of antigen concentrations in vitro.

FIG. 8B shows the half-life of SIINFEKL:$K^b$ complexes on these cells. Primary Langerhans cells obtained from 72 hr ear skin explants were incubated with 100 nM SIINFEKL as above, washed extensively and re-incubated in media lacking SIINFEKL. At various times thereafter, an aliquot of cells was removed, stained and analyzed as above. The results demonstrate that the half-life of SIINFEKL:$K^b$ complexes on mature primary Langerhans cells in vitro is approximately 40 hrs, which is considerably longer than that estimated from other kinds of assays for MHC class I:peptide complexes on dendritic cells (Ruedl et al. 2000 *J. Immunol.* 165:4910–4916; Cella et al. 1999 *J. Exp. Med.* 189:821–829).

Figure 9:
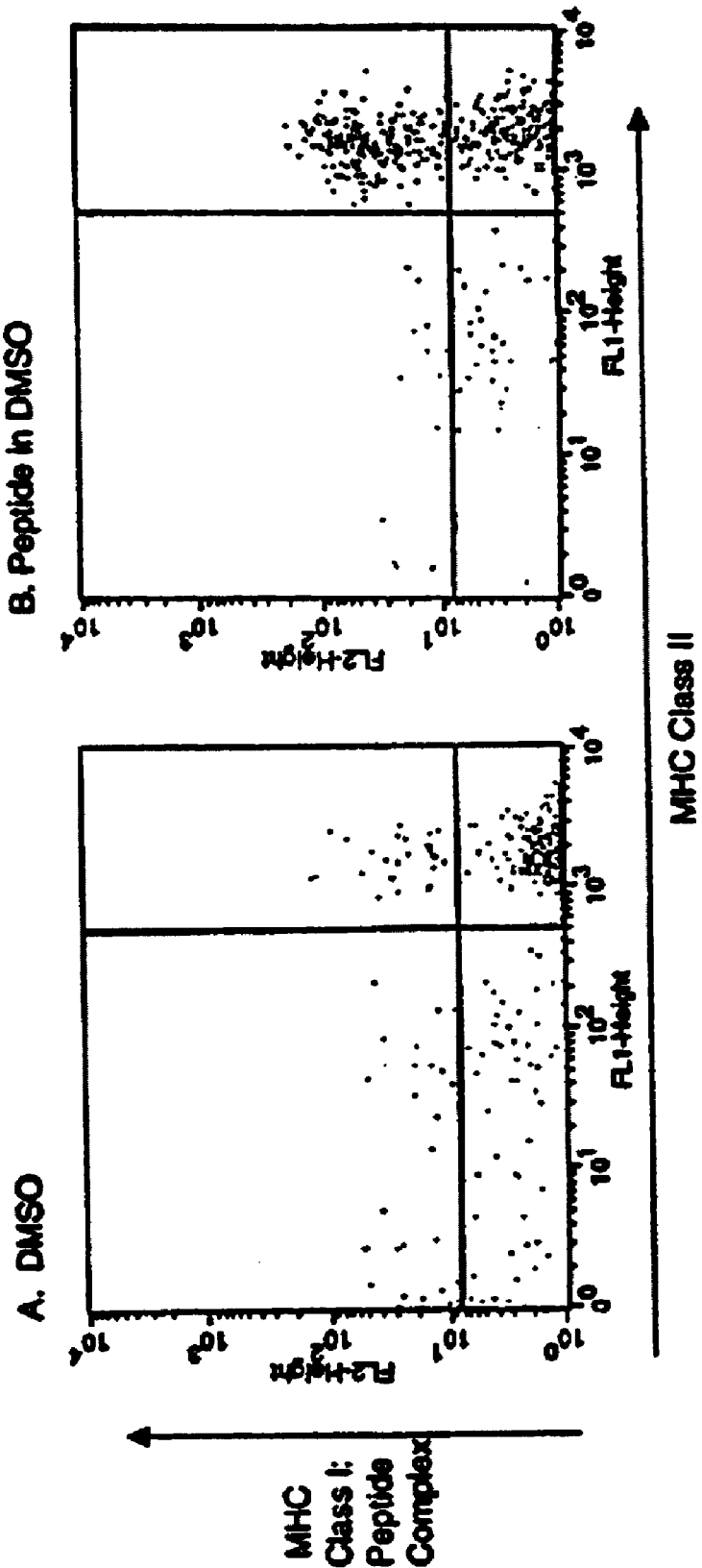
FIG. 9 illustrates the effect of topical delivery of a peptide antigen using ultrasound, followed by topical application of a chemical inducer of dendritic cell migration/maturation in vivo.

A Peptide Antigen can Be Delivered Topically using Low Frequency Ultrasound and Followed by a Chemical Inducer of Langerhans Cell Migration and Maturation FIG. 9 illustrates the effect of delivering a peptide antigen (SIINFEKL) into the skin via ultrasound, followed by topical application of dibutyl phthalate and acetone to maximize the induction of dendritic cell migration and maturation. SIINFEKL (240 μg) in DMSO, or DMSO alone, was applied to the shaved abdominal skin of C57BL/6 mice and covered with a hydrogel, into which was inserted a 13 mm diameter ultrasound transducer. Ultrasound was applied at 20 kHz and 1.6 W/cm$^2$, in 1 second pulses every 2 seconds for 6 minutes, for a total ultrasound dose of 288 J/cm$^2$. Two hours later, a 50:50 v/v solution of acetone and dibutyl phthalate was applied topically to the same area. Two days later, the skin draining inguinal lymph nodes were removed and the cells analyzed by immunofluorescent flow cytometry.

The antigen-bearing dendritic cells that had migrated to the draining lymph node are shown in the upper right quadrant of each dot plot. The dendritic cells in the lymph node were identified by their characteristic light scatter properties and exceptionally high surface expression of MHC class II (FL1), while the antigenic epitope was detected using the $K^b$:SIINFEKL-specific mAb 25-D1.16 (FL2), as described above. The absolute number of antigen-bearing immigrant dendritic cells per lymph node is presented in Table I.

TABLE I

Antigen-bearing Dendritic Cells in Lymph Nodes after Ultrasound Application of Soluble Peptide followed by Migration Inducer

| Treatment | Total Cells per Lymph Node | Dendritic Cells per Lymph Node | $K^b$:SIINFEKL$^+$ DC per LymphNode | Enhancement |
|---|---|---|---|---|
| DMSO | 5.3 × 10$^6$ | 64,236 | 2,862 | 1× |
| SIINFEKL in DMSO | 5.6 × 10$^6$ | 51,968 | 13,216 | 5× |

The frequency of dendritic cells in the inguinal lymph nodes of untreated C57BL/6 mice in the inventor's animal facility is 4,636 (SD 1,796) dendritic cells per node. The results shown in FIG. 9A provide dramatic evidence that this topical method to induce dendritic cell migration/maturation causes large numbers of dendritic cells (~60,000) to enter the draining lymph node, even in the absence of any antigen. Evidence that the dendritic cells induced to migrate from the periphery by this procedure are phenotypically mature includes their very high surface expression of MHC class II (see FL1), as well as their expression of CD44, alpha 4 integrin, ICAM-1, LFA-3, B7-1, B7-2, and CD40 (data not shown). Hence, we refer to agents of this class as "migration/maturation inducers". It is well established in the immunology literature that dendritic cells with this phenotype are functionally mature and potent stimulators of T cell activation (Banchereau and Steinman 1998 *Nature* 392:245–252), and that Langerhans cells induced to emigrate from the epidermis are functionally mature on entry into the lymph node and able to activate naive T cells to the antigens brought with them (Udey 1997 *Clin. Exp. Immunol.* 107 (Suppl. 1):6–8).

Although mAb 25-D1.16 is specific for SIINFEKL:$K^b$, similar to the findings of others (Porgador et al. 1997 *Immunity* 6:715–726), we found that some lymph node dendritic cells (2,862) induced to migrate and mature in the absence of SIINFEKL (FIG. 9A and Table I) displayed background staining with this mAb that was not apparent on comparable cells obtained in vitro (FIG. 8A). Background staining with this mAb requires $K^b$ expression and represents cross-reactivity with $K^b$ molecules occupied with an unknown endogenous peptide (Porgador et al. 1997 *Immunity* 6:715–726). Nonetheless, Langerhans cells induced to migrate to the lymph node after ultrasound-mediated topical exposure to SIINFEKL (FIG. 9B and Table I) contained five times as many cells (13,216) reactive with this mAb. These results provide quantitative evidence that this topical method of antigen delivery, combined with chemical induction of dendritic cell migration and maturation, results in large numbers of antigen-bearing dendritic cells in the draining lymph node.

Previous studies in the inventor's laboratory with topically applied fluorescein isothiocyanate (FITC) had demonstrated that the peak of epidermal Langerhans cell immigration into the skin-draining lymph node occurs approximately 48 hrs after topical delivery of migration/maturation inducers (see e.g., FIG. 2). Thus, an issue for the efficacy of topical vaccines delivered to epidermal Langerhans cells is the half-life in vivo of peptide:MHC class I complexes generated on immature Langerhans cells after exposure to peptides in the epidermis. The half-life of peptide:MHC class I complexes on mature Langerhans cells in vitro was ~40 hrs (FIG. 8B). Cella et al. reported a half-life of only about 10 hrs for peptide:MHC class I complexes on dendritic cells obtained from human peripheral blood precursors (Cella et al. 1999 *J. Exp. Med.* 189:821–829). Likewise, Ruedl et al. reported that a class I peptide delivered to the skin of mice was presented by draining lymph node dendritic cells for only one day (Ruedl et al. 2000 *J. Immunol.* 165:4910–4916). By contrast, the results shown in FIG. 9B establish that the half-life in vivo of peptide:MHC class I complexes generated on immature epidermal Langerhans cells by the present method is sufficient to permit these cells to accumulate in the draining lymph node for T cell activation 48 hrs later.

The preceding experiment, however, did not permit assignment of a half-life in vivo, because the amount of peptide transported across the stratum corneum was unknown. In an effort to determine an accurate half-life, we needed to know the amount of peptide to which the Langerhans cells were exposed in the epidermis. To this end, we attempted to bypass the stratum corneum and deliver a known amount of peptide directly into the epidermis. The results of that and subsequent experiments were unexpectedly revealing and became a basis for the present improvement to our earlier-filed patent application.

Figure 10:
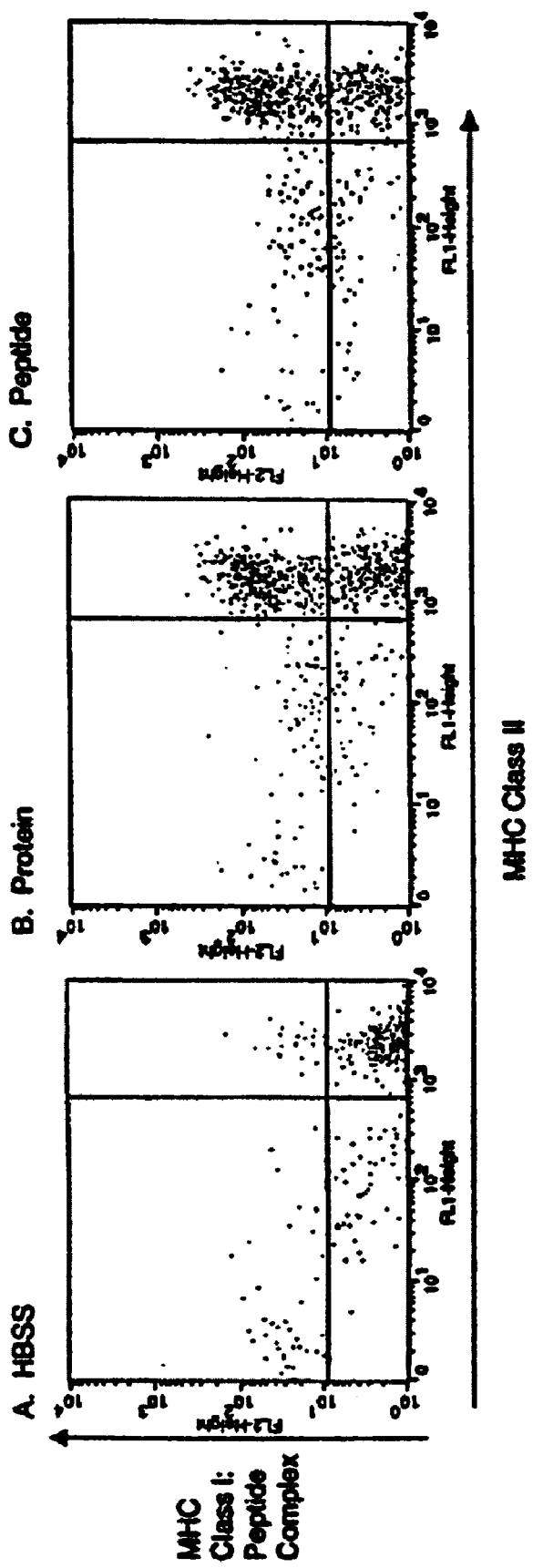
FIG. 10 illustrates the effect of injecting a soluble protein antigen or peptide antigen into mice, followed by topical application of an effective inducer of dendritic cell migration/maturation.

Protein and Peptide Antigens Injected Through the Skin can be Transported to the Lymph Node by Migrating Dendritic Cells FIG. 10 illustrates the effect of injecting: A) 20 µl of Hank's balanced salt solution (HBSS); B) 20 µl of a 0.5 mM solution of chicken ovalbumin protein (OVA) in HBSS; or, C) 20 µl a 0.5 mM solution of the $OVA_{257-264}$ peptide (SIINFEKL) in HBSS, divided equally between two contralateral sites in the shaved abdominal skin of mice. The extracellular fluid space in the abdominal skin of mice seemed unable to contain more than about 10 µl, so only 200 µg of OVA protein or 4.8 µg of SIINFEKL peptide were injected per site. Even so, it is not clear that these injections were limited to the skin. The injections were followed 2 hours later by topical application of dibutyl phthalate and acetone to the abdominal skin. The antigen-bearing dendritic cells that had migrated to the draining lymph node two days later were analyzed as described above and are shown in the upper right quadrant of each dot plot.

The data in Table II show that the injection of HBSS followed by topical induction of immature dendritic cell migration/maturation (FIG. 10A) resulted in approximately the same number of immigrant dendritic cells in the draining lymph node (~56,000) and the same extent of background staining with 25-D1.16 (2,016) as seen after ultrasound treatment with DMSO followed by dibutyl phthalate and acetone (FIG. 9A). Surprisingly, however, the injection of either OVA protein or SIINFEKL peptide, followed by topical induction of immature dendritic cell migration, resulted in a much larger increase, 31-fold and 44-fold respectively, in the number of antigen-bearing dendritic cells found in the draining lymph nodes two days later. This seemed remarkable given that the molar dose of injected antigen was only 2% of that applied to the skin and delivered across the stratum corneum by ultrasound. It appeared that this procedure had enabled the immature dendritic cells that were induced to emigrate from the epidermis, to capture the injected antigen while en route to the lymph node. However, this experimental design did not address the role, if any, of the migration inducer.

TABLE II

Antigen-bearing Dendritic Cells in Lymph Nodes after Injection of Soluble Protein or Peptide followed by Migration Inducer

| Treatment | Total Cells per Lymph Node | Dendritic Cells per Lymph Node | $K^b$:SIINFEKL$^+$ DC per LymphNode | Enhancement |
|---|---|---|---|---|
| HBSS | $4.8 \times 10^6$ | 60,384 | 2,016 | 1× |
| OVA | $8.8 \times 10^6$ | 137,456 | 61,424 | 31× |
| SIINFEKL | $1.1 \times 10^7$ | 162,628 | 89,598 | 44× |

Role of the Inducer of Dendritic Cell Migration and Maturation

Figure 11:
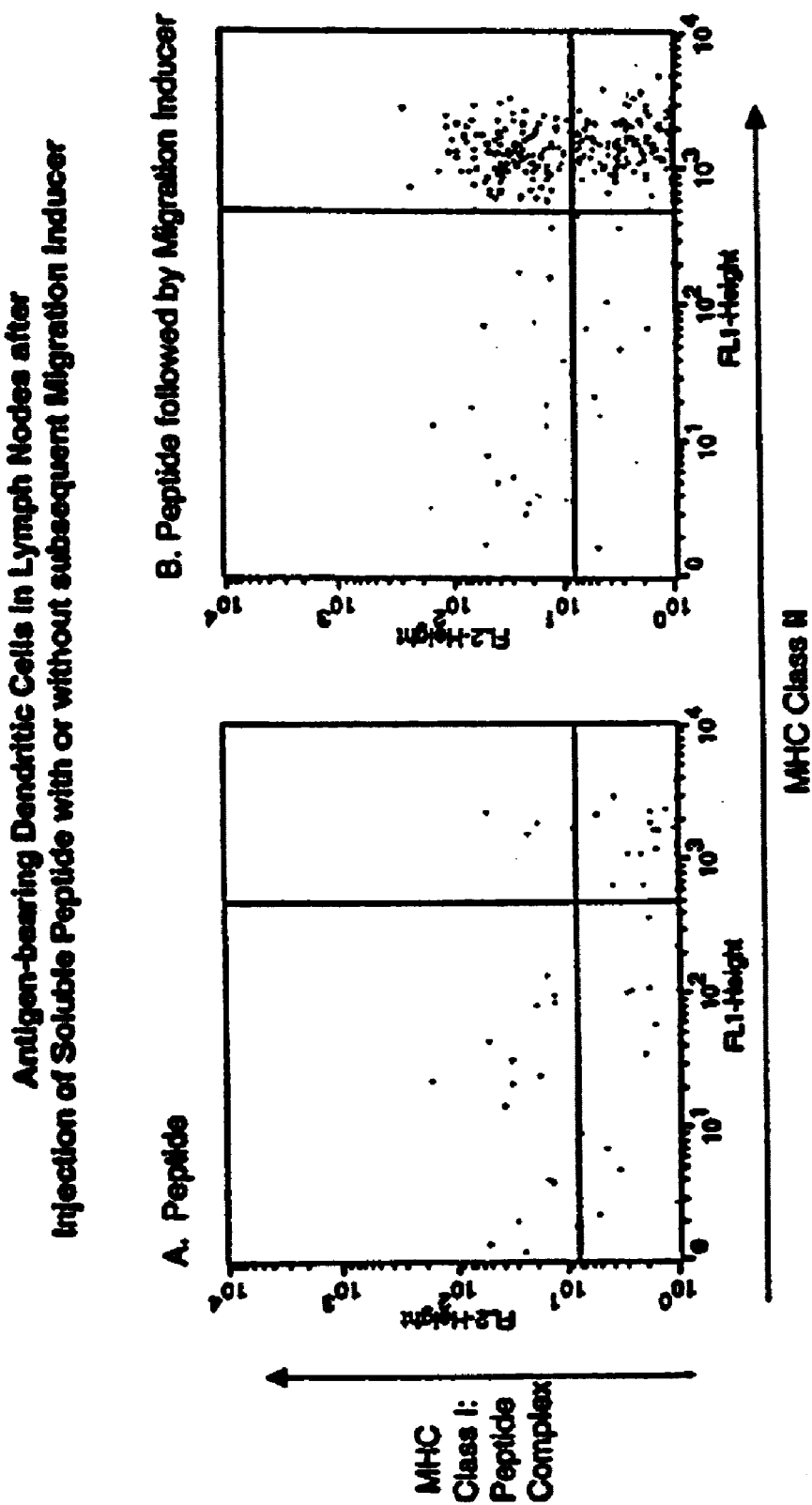
FIG. 11 shows the role of the inducer of dendritic cell migration/maturation for achieving the desired effect.

FIG. 11 illustrates the role of applying an effective inducer of dendritic cell migration/maturation in achieving the desired result. SIINFEKL peptide antigen (a total of 144 µg in 150 µl HBSS) was injected in a divided dose in two contralateral sites in and through the shaved abdominal skin of mice. This was followed 2 hrs later by: A) no further treatment, or B) topical application of dibutyl phthalate and acetone to the abdominal skin. The antigen-bearing dendritic cells that had migrated to the draining lymph node two days later are shown in the upper right quadrant of each dot plot. The absolute number of antigen-bearing immigrant dendritic cells per lymph node is shown in Table III.

TABLE III

Antigen-bearing Dendritic Cells in Lymph Nodes after Injection of Soluble Peptide with or without subsequent Migration Inducer

| Treatment | Total Cells per Lymph Node | Dendritic Cells per Lymph Node | $K^b$:SIINFEKL$^+$ DC per LymphNode | Enhancement |
|---|---|---|---|---|
| SIINFEKL alone | $6.3 \times 10^6$ | 3,024 | 504 | 1× |
| SIINFEKL + Migration Inducer | $8.6 \times 10^6$ | 55,912 | 22,239 | 44× |

With reference to FIG. 11 and Table III, the number of dendritic cells found in the inguinal lymph nodes of mice injected 2 days previously with SIINFEKL peptide without further treatment (3,024) is within the normal range found in untreated mice, i.e., 4,636 (SD 1,796). In other words, the injection of a large fluid volume containing a large amount of peptide antigen induced no detectable migration of dendritic cells to the draining lymph node. That these injections resulted in wide dispersion of the antigen was confirmed by microscopic examination after comparable injections of Evans Blue dye. The dye was found to permeate the epidermis, dermis, subcutaneous fat and outer surface of the peritoneal wall (data not shown). Nonetheless, the number of dendritic cells reacting with the monoclonal antibody detecting MHC class I:SIINFEKL complexes, found in the same lymph nodes (504), is less than the number of dendritic cells that were non-specifically stained with this reagent (2,016) shown in FIG. 10 (HBSS-injected mice). Thus, in spite of a large and widely disseminated dose of soluble peptide antigen, no detectable antigen-bearing Langerhans cells were induced to migrate to the draining lymph node, and no detectable peptide reached the lymph node for uptake by the resident dendritic cells. These results demonstrate why subunit vaccines that are not pro-inflammatory, and fail to induce the migration of peripheral dendritic cells, may lack sufficient immunogenicity to be clinically useful.

By contrast, the number of dendritic cells (55,912) found in mice injected 2 days previously with SIINFEKL peptide, followed by topical application of the migration/maturation inducer, represents an 18.5-fold increase in the total number of dendritic cells per lymph node. More importantly, the application of the effective migration inducer resulted in 22,239 antigen-bearing dendritic cells per lymph node, representing a 44-fold increase over that obtained following antigen injection without an effective migration/maturation inducer.

Density of Peptide:MHC Complexes Found on the Dendritic Cells Induced to Migrate from the Periphery by this Procedure As stated previously, whether mature antigen-bearing dendritic cells will be encountered by and activate naive T cells in the lymph node is likely to depend not only on the number of antigen-bearing dendritic cells that enter the node, but also on the density of MHC:peptide complexes expressed on their membranes. To estimate the density of peptide:MHC complexes on the immigrant dendritic cells generated by this procedure, we compared the fluorescence intensity of various cell populations detected by the peptide:MHC-specific mAb, 25-D1.16, using identical staining conditions and flow cytometer settings. The results are shown in Table IV, providing the number of specific peptide:MHC complexes expressed on the plasma membrane of dendritic cells after various treatments in vitro or in vivo.

The tumor cell, E.G7-OVA, is the C57BL/6 EL4 thymoma transfected with the complete gene for chicken ovalbumin (OVA). The $K^b$:SIINFEKL complex is processed naturally and expressed on the plasma membrane of E.G7-OVA. The number of those complexes expressed per cell has been measured independently by two different laboratories and reported to be 88 (Rotzschke et al. 1991 *Eur. J. Immunol.* 21:2891–2894) and 90 (Malarkannan et al. 1995 *J. Exp. Med.* 182:1739–1750). Therefore, the fluorescence intensity of E.G7-OVA could be used as a standard by which to estimate the number of $K^b$:SIINFEKL complexes expressed on the dendritic cell populations identified in the present study. The immigrant lymph node dendritic cells shown in FIG. 9 expressed a median number of 633 $K^b$:SIINFEKL complexes per cell, while the immigrant lymph node dendritic cells generated by the procedure described in FIG. 10 expressed a median number of 860 $K^b$:SIINFEKL complexes per cell.

TABLE IV

NUMBER of SIINFEKL:$K^b$ COMPLEXES per CELL

| Cell Type | SIINFEKL[a] | Median Specific Fl. Intensity[b] | Median No. of Complexes/Cell[c] |
|---|---|---|---|
| E.G7-OVA | endogenous | 4.5 | 89[d] |
| Langerhans cells[e] | 0.1 nM in vitro | 12 | 240 |
| " | 1.0 nM in vitro | 80 | 1,600 |
| " | 10 nM in vitro | 209 | 4,180 |
| " | 100 nM in vitro | 558 | 11,160 |
| " | 1 μM in vitro | 760 | 15,200 |
| Langerhans cells[f] | 4.8 μg injected | 43 | 860 |
| " | 240 μg ultrasound[g] | 32 | 633 |

[a]Amount and source of SIINFEKL peptide to which the cells were exposed.
[b]The median fluorescence intensity of E.G7-OVA cells stained with mAb 25-D1.16, minus the non-specific staining of the same cell population in the absence of 25-D1.16; or, in the case of Langerhans cells in vitro, the median fluorescence intensity of cells incubated with SIINFEKL and stained with 25-D1.16, minus the median fluorescence intensity of cells incubated in the absence of SIINFEKL and stained with 25-D1.16; or, in the case of immigrant Langerhans cells in vivo, minus the median fluorescence intensity of the negative Langerhans cells in the same sample.
[c]The median number of SIINFEKL:$K^b$ complexes per cell was calculated from the median specific fluorescence intensity detected on E.G7-OVA cells, using the same reagents and flow cytometer settings. Based on the reported number of SIINFEKL:$K^b$ complexes expressed on E.G7-OVA cells, 1 fluorescence intensity unit = 20 SIINFEKL:$K^b$ complexes.
[d]Rotzschke, O. et al. (48) reported 88 SIINFEKL:$K^b$ complexes per E.G7-OVA cell. Malarkannan, S. et al. (49) reported 90 SIINFEKL:$K^b$ complexes per E.G7-OVA cell.
[e]Primary Langerhans cells, that had emigrated from skin explants during 72 hrs in vitro, were incubated for 1.5 hrs with SIINFEKL, washed and analyzed immediately.
[f]Immigrant Langerhans cells obtained from inguinal lymph nodes 48 hrs after treatment in vivo.
[g]The ultrasound used was 20 kHz, 1.6 W/cm$^2$, 1 sec pulse/2 sec for 6 min., or 288 J/cm$^2$.

It has been shown by various studies in different laboratories (see e.g., Reay et al. 2000 *J. Immunol.* 164:5626–5634 and Wherry et al. 1999 *J. Immunol.* 163:3735–3745) that approximately 200–400 MHC:peptide complexes provide a desired level of T cell activation. Therefore, the results shown in FIGS. 10 and 11 and Table IV indicate that the density of specific peptide:MHC complexes on antigen-bearing dendritic cells found in the lymph node subsequent to the disclosed treatment would be competent to induce a primary immune response to the antigen(s). Moreover, the data demonstrate that the application of an effective means to induce dendritic cell migration/maturation is a potent immunologic adjuvant for the administration of antigens that would otherwise be ignored by the immune system (see FIG. 11A and Table III).

The protein and peptide forms of the antigen shown in FIG. 10 were injected in molar equivalents and resulted in a similar frequency of MHC class I:SIINFEKL-bearing dendritic cells in the lymph nodes. Furthermore, the density of the MHC class I:SIINFEKL complexes per dendritic cell (FL2 fluorescence intensity) was similar, whether the injected antigen was a synthetic peptide or the whole natural protein. These data show that the effect of this procedure is independent of the source of the antigen (i.e., endocytosed and processed or obtained by peptide exchange) and independent of its structural form. Thus, the invention is useful with antigen(s) from any source, for example but not limited to: prokaryotic or eukaryotic, viral, bacterial, fungal, protozoan, parasite and prion, natural, synthetic or recombinant, xenogeneic, allogeneic, syngeneic, or autologous. Moreover, the invention is useful with antigens in any structural form, for example but not limited to: DNA, RNA, protein, peptide, carbohydrate, lipid, organic, inorganic, and any combination thereof.

Figure 12:
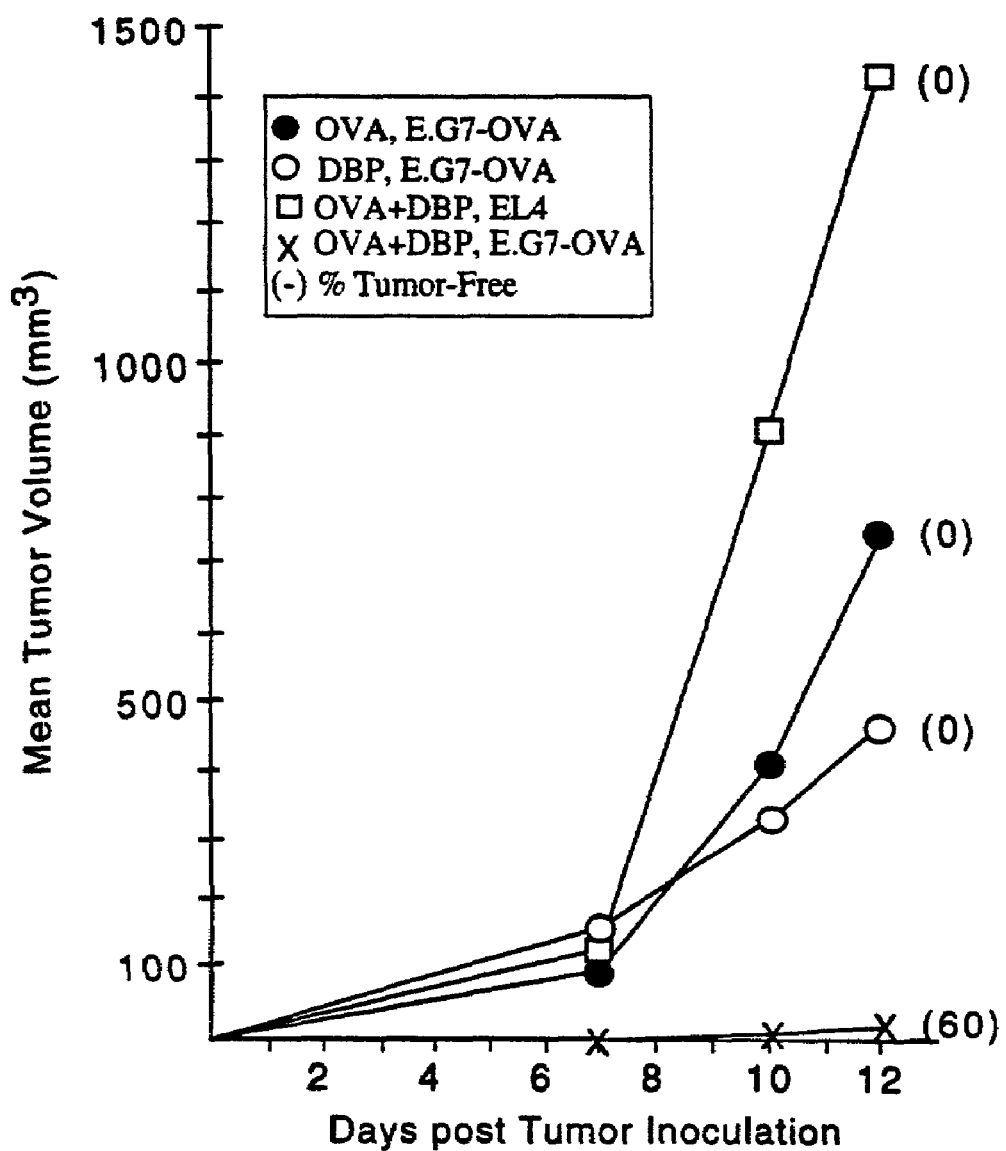
FIG. 12 shows the induction of tumor-specific immunity by injection of tumor-associated protein antigen followed by topical application of a dendritic cell migration/maturation inducer.

To confirm the immunogenicity of the disclosed treatment, groups of 10 C57BL/6 mice were injected with 50 μl of 1.25 mM OVA protein in HBSS, with HBSS alone, or with nothing. This was followed an hour later by topical application of DBP in acetone or with nothing. One month later, the mice were inoculated subcutaneously with 5×10$^5$ EL4 tumor cells or with 5×10$^5$ E.G7-OVA tumor cells and subsequent tumor growth was measured. As illustrated in FIG. 12, only one combination resulted in tumor protection; namely, injection of OVA protein followed by DBP and acetone and subsequent inoculation with the OVA-transfected tumor cell line, E.G7-OVA.

The data shown in FIGS. 10–12 also demonstrate that the adjuvant effect of this procedure can be achieved even when the delivery of the antigen and the application of the effective dendritic cell migration/maturation inducer are physically, spatially and temporally separated events. This would not have been predicted from our earlier results (see e.g., U.S. patent application Ser. No. 09/176,044), nor would it have been suggested by any prior art of which the inventor is aware. Moreover, the invention has immediate utility because it can be used to enhance the immunogenicity of existing vaccine formulations delivered by currently used methods. It could also enhance the immunogenicity of experimental vaccine formulations and delivery methods, such as, but not limited to, topical application of naked DNA (Fan et al. 1999 *Nature Biotech.* 17:870–872) or DNA incorporated into viral vectors (WO 00/22124) or other expression constructs (Irvine et al. 2000 *Nature Biotech.* 18:1273–1278).

The invention is conceived to be useful for antigen(s) delivered to the host by any means. The antigen could be delivered by penetration of the stratum corneum with needles (as shown in FIGS. 10–12) or by other commonly used invasive procedures. The antigen(s) can applied topically to the skin or mucous membranes, with (as shown in FIG. 9) or without a variety of penetration enhancers, such as but not limited to: chemical or biologic penetration enhancers, and penetration achieved by ultrasound, iontophoresis, electroporation, lasers, thermal effects, hydrostatic pressure or other physical means. Alternatively, dendritic cells could be exposed to the antigen(s) by infection or transfection, or by disruption of the stratum corneum using abrasion, chemical peels, lasers or other physical or chemical means described in the scientific and patent literature.

The disclosed procedure could also be used to induce the migration/maturation of immature dendritic cells from non-lymphoid organs, other than the skin or mucous membranes, to the lymph nodes draining those sites. This embodiment could be achieved by direct application of an effective migration/maturation inducer to such sites, or by delivering the inducer to those sites using indirect means well known to persons skilled in the art of drug delivery.

The Amount of Antigen Delivered to the Dendritic Cell is Independent of the Extent of the Migration Induced Table V shows the effect of different compositions of a dendritic cell migration/maturation inducer on the amount of cell-bound antigen on the dendritic cells that subsequently appear in the lymph node. The antigen employed was FITC and the procedure was identical to that used for the experiments depicted in FIG. 1. Namely, FITC at 5 mg/ml was dissolved in a 50:50 solution of acetone and the test agents for migration induction. The test agents used in this experiment were: dibutylfumarate (Agent #1); diisooctylmaleate (Agent #2); and dibutyl-D-tartarate (Agent #3). The inguinal lymph nodes were examined 48 hrs later for the presence of FITC+ and FITC-dendritic cells as detailed previously.

TABLE V

The Extent of Migration is Independent of the Amount of Antigen Delivered to the Dendritic Cell

| DC in Lymph Node | Migration Inducers | | |
|---|---|---|---|
| | Test Agent #1 | Test Agent #2 | Test Agent #3 |
| Antigen+ DC[a] | 4,242 | 5,340 | 14,175 |
| Amt. Antigen/DC[b] | 994 | 1032 | 364 |
| Total DC[c] | 10,088 | 7,927 | 29,050 |

[a]FITC + MHC class II$^{Hi}$ cells per lymph node.
[b]Amount of antigen/DC was determined by the mean fluorescence intensity (arbitrary units) of the dendritic cells.
[c]Total DC = FITC+ dendritic cells plus FITC− dendritic cells per lymph node.

The data demonstrate that the amount of antigen delivered to the dendritic cell is independent of the extent of migration induced. While it has been hypothesized that delivery of an MHC-binding peptide antigen to epidermal Langerhans cells may be sufficient to induce their migration to draining lymph nodes (Becker 1994 Virus Genes 9:33–45), to our knowledge this hypothesis has not been tested, and we have found no evidence to indicate that it is true. For example, fluorescein isothiocyanate is a small haptenic antigen that can penetrate the skin (as seen by immunofluorescence histology) when applied in acetone and a lipophilic penetration enhancer such as olive oil (data not shown). But, this induces little dendritic cell migration to the lymph node beyond that induced by simply shaving the skin. Similarly, the injection of a large quantity of peptide antigen, demonstrably able to bind to the MHC class I molecules on the recipients dendritic cells, resulted in no detectable peptide: MHC complexes on the dendritic cells found in the lymph node draining the injection site (FIG. 11A and Table III). Therefore, exposure of immature dendritic cells to antigen per se is not sufficient to induce their maturation and migration to draining lymph nodes in numbers sufficient to be useful for vaccines. Conversely, it is clear from the data shown in FIGS. 9A and 10A and Tables I and II, that significant levels of dendritic cell migration to the lymph node can be induced in the absence of any known antigen, as when an effective inducer of dendritic cell migration was applied topically after an injection of sterile HBSS lacking Phenol Red.

On the other hand, some antigen preparations could contain an inducer of dendritic cell migration. This would obtain naturally if the antigen is also pro-inflammatory and induces dendritic cell migration, e.g., certain microorganisms or their products such as LPS. This might also be achieved by synthetic design, if the antigen is coupled to an endogenous mediator of dendritic cell migration such as TNF-alpha or IL-1. In the vast majority of cases, however, delivery of an antigen to peripheral immature dendritic cells is not a sufficient stimulus for the desired adjuvant effect. Similarly, it is not sufficient and may be erroneous to presume that any substance or procedure that enhances an immune response does so by effectively inducing dendritic cell migration.

One skilled in the art of immunology would appreciate that the disclosed invention could be used with an antigen that is an agonist, partial agonist or antagonist of antigen-specific receptors on cells of the immune response (Sloan-Lancaster and Allen 1996 Annu. Rev. Immunol. 14:1; Alam et al. 1999 Immunity 10:227). By obvious extension, the invention could be used in conjunction with substances that are agonists or antagonists of other receptors on immune system cells, that are not antigen-specific but function to activate or suppress a particular type of immune response. Using a combination of methods well known to those in the field, the invention could be practiced to achieve or enhance the activation, inhibition, prolongation or cessation of an immune response.

Figure 13:
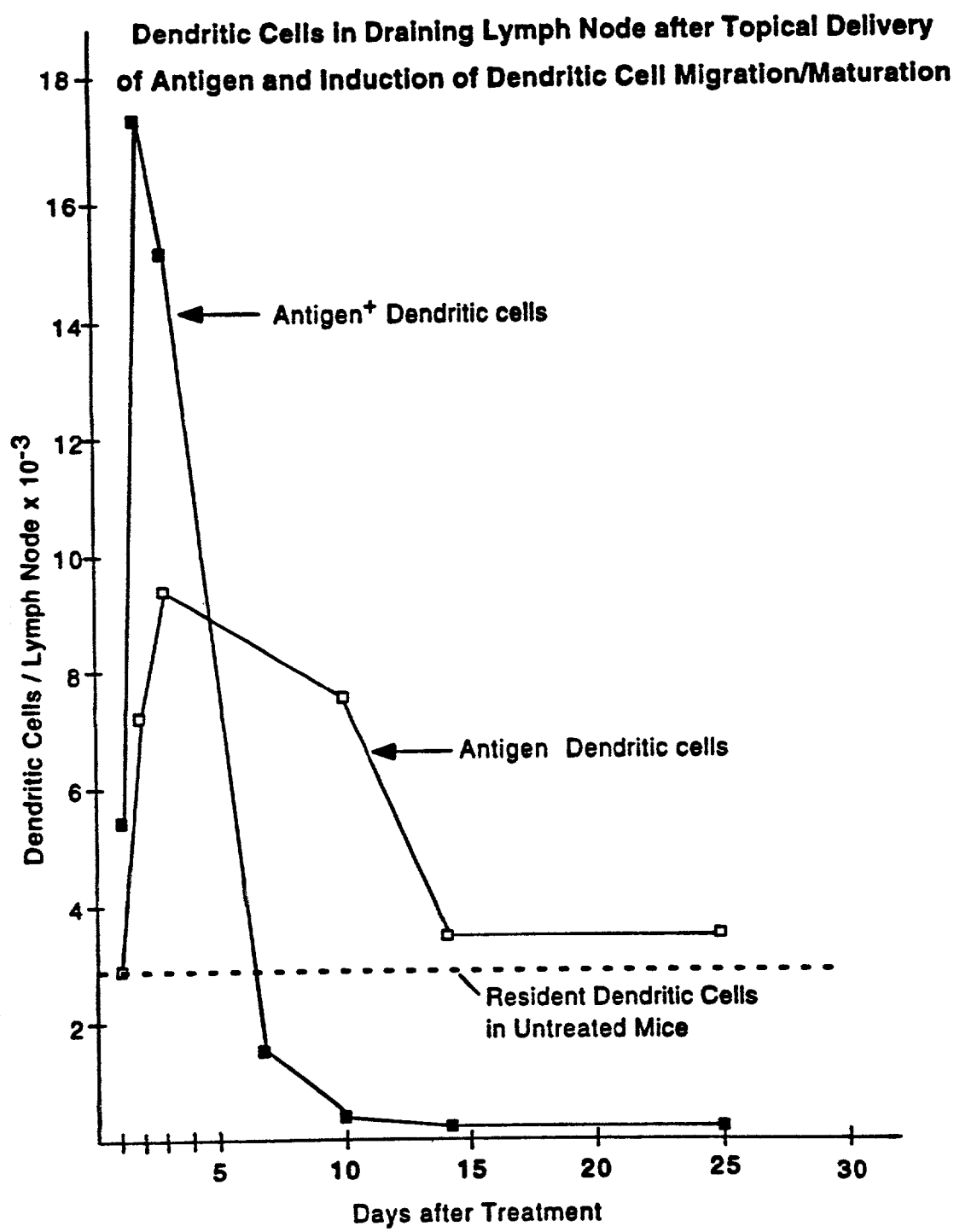
FIG. 13 shows that the effective induction of dendritic cell migration to a lymph node is followed by a prolonged influx of non-antigen-bearing dendritic cells into the same lymph node.
Figure 14:
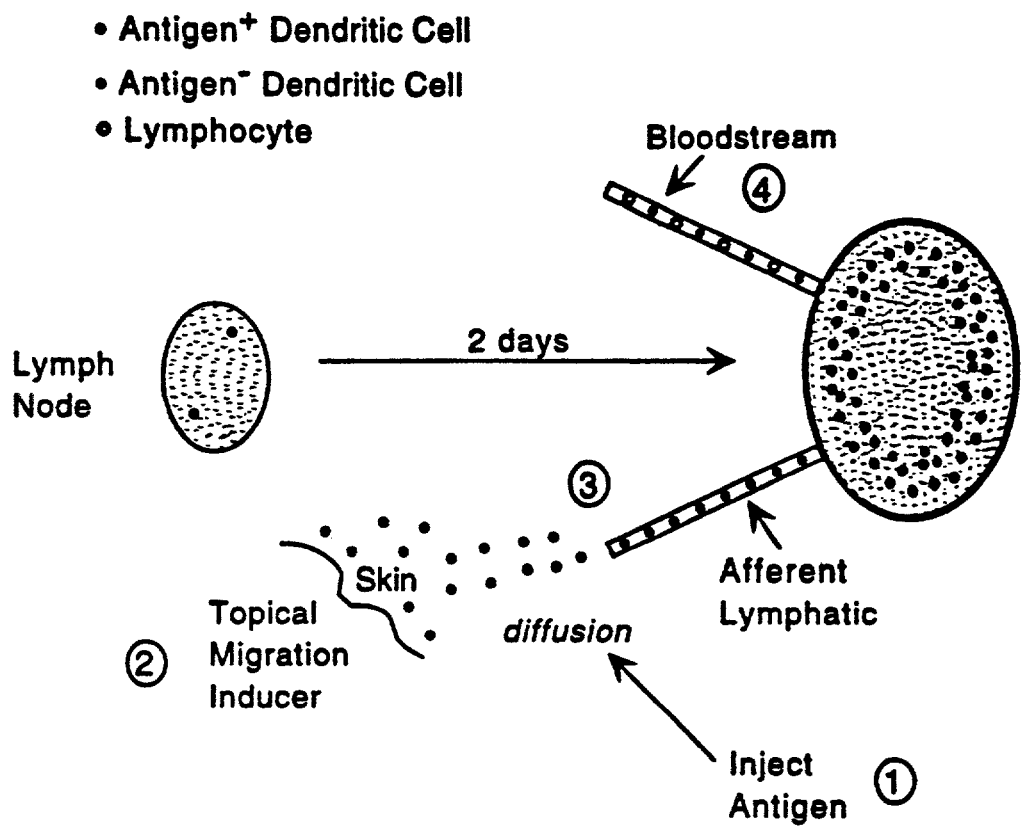
FIG. 14 illustrates the overall adjuvant effects of inducing the migration and maturation of immature dendritic cells on the immunogenicity of an introduced antigen, using the data shown in FIG. 11 as an example.

The Disclosed Procedure Induces the Subsequent Influx of Antigen-Free Dendritic Cells and Peripheral Blood Leukocytes into the Draining Lymph Node The data in FIG. 13 demonstrate that the effective induction of dendritic cell migration to a lymph node is followed by a prolonged influx of non-antigen-bearing dendritic cells into the same lymph node. This effect is also apparent from the data shown in Tables I, II and III and in U.S. patent application Ser. No. 09/176,044. The increase in overall cellularity of the draining lymph node shortly after the induction of dendritic cell migration and maturation (see FIG. 3) may be largely the result of an influx of peripheral blood leukocytes (Tedla et al. 1998 J. Immunol. 161:5663–5672), rather than expansion of antigen-specific immune system cells, as the effect occurs too rapidly to be accounted for by antigen-specific cell division alone.

This secondary influx of dendritic cells and other leukocytes via the peripheral blood is anticipated to increase the adjuvant effect that results from effective induction of the migration of immature dendritic cells to the site of antigen deposition or diffusion, while en route to the draining lymph node. This conceptualization of the invention is depicted in FIG. 13, using the data obtained in the experiment shown in FIG. 11. Both the initial immigration of dendritic cells into the draining lymph node, and the secondary influx of non-antigen-bearing dendritic cells and blood-borne leukocytes, is dependent upon the application of an effective migration/maturation inducer.

The Induction of Immature Dendritic Cell Migration and Maturation can be Repeated without Loss of Efficacy The data shown in Table VI demonstrate that the effective induction of dendritic cell migration and maturation can be repeated as early as 14 days after a prior application to the same site, with full restoration of the response. The antigen used was FITC, which was applied topically to the shaved abdominal skin of C57BL/6 mice at 5 mg/ml in a 50:50 solution of dibutyl phthalate and acetone. Each of the applications was identical, with half of the mice in each group receiving the first application only (none) and half receiving the first application followed by a second application at the specified interval (14 days or 21 days) after the first application. The inguinal lymph node cells were examined by flow cytometry for FITC+ dendritic cells, as detailed previously, 48 hrs after each treatment.

Two weeks is not necessarily the shortest interval in which the procedure can be repeated, but it was the earliest time point that could be used experimentally. Prior to that time, residual antigen-bearing dendritic cells can still be found in draining lymph nodes, obscuring accurate quantitation of newly immigrant, antigen-bearing dendritic cells.

TABLE VI

Immature Dendritic Cells are Fully Restored to the Peripheral Site within 14 Days after Treatment

| Day of 1st Treatment | Day of 2nd Treatment | Day of Assay | Cells per Lymph Node | Antigen-bearing Dendritic Cells/Node |
|---|---|---|---|---|
| 1 | none | 2 | $6.76 \times 10^6$ | 64,220 |
| 1 | 14 | 16 | $1.28 \times 10^7$ | 99,840 |
| 1 | none | 16 | $4.52 \times 10^6$ | 1,776 |
| 1 | 21 | 23 | $6.93 \times 10^6$ | 49,203 |
| 1 | none | 23 | $3.87 \times 10^6$ | 0 |

The repeatability of the disclosed procedure may be important for its utility as an adjuvant for DNA vaccines, or for other forms of antigen that result in prolonged expression and/or release of the antigen. That is, a single administration of a vaccine that results in long-term antigen expression could be accompanied by repeated induction of dendritic cell migration and maturation at appropriate time intervals, in order to achieve a booster effect similar to or greater than that obtained by multiple immunizations.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method for vaccinating a mammal against a target antigen, comprising:
   introducing into the mammal by disrupting the stratum corneum an effective dose of the target antigen or an epitope(s) thereof; and
   administering to the mammal a topical treatment which in the absence of antigen is sufficient to increase the number of dendritic cells migrating to a lymphoid organ, wherein the topical treatment comprises a lipophilic molecule of <500 daltons capable of traversing the stratum corneum and having the formula selected from the following formulas:

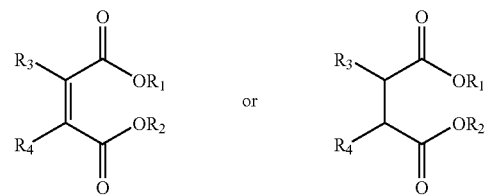

wherein $R_1$ and $R_2$ are selected independently from the group consisting of alkyl side chains containing 1 to 16 carbon atoms, $C_1$ to $C_{16}$ substituted alkyl, $C_3$ to $C_{10}$ cycloalkyl, $C_3$ to $C_{10}$ substituted cycloalkyl, $C_2$ to $C_{10}$ alkenyl, $C_2$ to $C_{10}$ substituted alkenyl, $C_2$ to $C_{10}$ alkynyl, and $C_2$ to $C_{10}$ substituted alkynyl;

wherein $R_3$ and $R_4$ are independently hydrogen atom, hydroxy group, or are linked to form a cyclic ring, which comprises unsaturated $C_6$ cycloalkyl.

2. A method for vaccinating a mammal against a target antigen, comprising:
   introducing into the mammal by disrupting the stratum corneum an effective dose of the target antigen or an epitope(s) thereof; and
   administering to the mammal a topical treatment which in the absence of antigen is sufficient to increase the number of dendritic cells migrating to a lymphoid organ, wherein the topical treatment comprises a lipophilic molecule capable of traversing the stratum corneum, and wherein the lipophilic molecule is dibutyl phthalate or camphor.

3. The method of claim 1, wherein the $R_1$ and $R_2$ groups are identical $C_1$ to $C_6$ alkyl moieties.

4. The method of claim 1, wherein $R_1$ and $R_2$ are $(CH_2)_3$—$CH_3$.

5. A method, for vaccinating a mammal against a target antigen, comprising:
   introducing into the mammal by disrupting the stratum corneum an effective dose of the target antigen or an epitope(s) thereof; and
   administering to the mammal a topical treatment which in the absence of antigen is sufficient to increase the number of dendritic cells migrating to a lymphoid organ, wherein the topical treatment comprises a lipophilic molecule capable of traversing the stratum corneum, and wherein the lipophilic molecule is selected from the group consisting of dibutyl phthalate, dibutyl-D-tartrate, N,N-diethyl-toluamide, dibutylfumarate, di(2-ethylhexyl)fumarate, diisooctylmaleate, diethylhexylmaleate, diisooctylfumarate, benzoic acid, biphenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, and diethylmethylphthalate.

6. The method of claim 1, 2 or 5, wherein the lipophilic molecule has an oil/water partition coefficient >1.

7. The method of claim 1, 2 or 5, wherein the lipophilic molecule has an oil/water partition coefficient of between about 10 and about $10^6$.

8. The method of claim 1, 2 or 5, wherein the topical treatment further comprises an organic solvent.

9. The method of claim 8, wherein the organic solvent is acetone.

10. The method of claim 1, 2 or 5, wherein the introducing step further comprises transferring cells comprising the target antigen or epitope(s) thereof.

11. The method of claim 9, wherein the target antigen is selected from the group consisting of a virus, a bacterium, a fungus, and a parasite.

12. The method of claim 1, 2 or 5, wherein the introducing step further comprises injecting the target antigen or epitope(s) thereof.

13. The method of claim 12, wherein the injection is made via a route selected from the group consisting of intraepidermal, intradermal, subcutaneous, intramuscular, intravascular, or into a specific organ.

14. The method of claim 1, 2 or 5, wherein the topical treatment is sufficient to increase the number of dendritic cells in the lymphoid organ by a factor of about 2 to about 1000 times the number of resident dendritic cells in an untreated mammal.

15. The method of claim 14, wherein the number of dendritic cells in the lymphoid organ is increased by a factor of about 5 to about 100 times the number of resident dendritic cells in an untreated animal.

16. The method of claim 1, 2 or 5, wherein the target antigen is a tumor antigen.

17. A method for vaccinating a mammal against a target antigen, comprising:
   introducing into the mammal by injection an effective dose of the target antigen or an epitope(s) thereof; and
   administering to the mammal a topical treatment which in the absence of antigen is sufficient to increase the number of dendritic cells migrating to a lymphoid organ, wherein the topical treatment comprises ultrasound.

* * * * *

UNITED STATES PATENT AND TRADEMARK OFFICE
CERTIFICATE OF CORRECTION

| | | |
|---|---|---|
| PATENT NO. | : 7,229,621 B2 | Page 1 of 1 |
| APPLICATION NO. | : 09/809158 | |
| DATED | : June 12, 2007 | |
| INVENTOR(S) | : Carol O. Cowing | |

It is certified that error appears in the above-identified patent and that said Letters Patent is hereby corrected as shown below:

Title Page
Col. 2 (Other Publications), Line 42, Delete "Immunoloty" and insert -- Immunology --, therefor.

In column 1, line 40, Delete "J" and insert -- J. --, therefor.

In column 5, line 7-8, Delete "bihenylmaleate," and insert -- biphenylmaleate, --, therefor.

In column 18, line 39, Delete "bihenylmaleate," and insert -- biphenylmaleate, --, therefor.

In column 20, line 23, Delete "in vitro" and insert -- In Vitro --, therefor.

In column 21, line 20, Delete "can" and insert -- Can --, therefor.

In column 21, line 21, Delete "using" and insert -- Using --, therefor.

In column 27, line 33, Delete "FITC-dendritic" and insert -- FITC- dendritic --, therefor.

In column 27, line 67, Delete "recipients" and insert -- recipient's --, therefor.

In column 30, line 42, In Claim 5, delete "method," and insert -- method --, therefor.

In column 31, line 8, In Claim 11, delete "claim 9," and insert -- claim 10, --, therefor.

Signed and Sealed this

Eighteenth Day of December, 2007

JON W. DUDAS
*Director of the United States Patent and Trademark Office*